United States Patent
Schultz et al.

(10) Patent No.: US 6,992,284 B2
(45) Date of Patent: Jan. 31, 2006

(54) ION MOBILITY TOF/MALDI/MS USING DRIFT CELL ALTERNATING HIGH AND LOW ELECTRICAL FIELD REGIONS

(75) Inventors: J. Albert Schultz, Houston, TX (US); Valeri Raznikov, Moscow (RU); Thomas F. Egan, Houston, TX (US); Michael V. Ugarov, Houston, TX (US); Agnes Tempez, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 0 days.

(21) Appl. No.: 10/969,643

(22) Filed: Oct. 20, 2004

(65) Prior Publication Data
US 2005/0109931 A1    May 26, 2005

Related U.S. Application Data

(60) Provisional application No. 60/512,825, filed on Oct. 20, 2003.

(51) Int. Cl.
*B01D 59/44*    (2006.01)

(52) U.S. Cl. .................. 250/287; 250/287; 250/292
(58) Field of Classification Search ................ 250/287, 250/292
See application file for complete search history.

(56) References Cited

U.S. PATENT DOCUMENTS

| | | | | | |
|---|---|---|---|---|---|
| 4,963,736 A | * | 10/1990 | Douglas et al. | ............. | 250/292 |
| 5,905,258 A | * | 5/1999 | Clemmer et al. | ........... | 250/287 |
| 6,107,628 A | * | 8/2000 | Smith et al. | ................ | 250/292 |
| 6,177,668 B1 | * | 1/2001 | Hager | ........................ | 250/282 |
| 6,730,904 B1 | * | 5/2004 | Wells | ........................ | 250/292 |
| 6,744,043 B2 | * | 6/2004 | Loboda | ...................... | 250/287 |
| 6,888,130 B1 | * | 5/2005 | Gonin | ........................ | 250/287 |

* cited by examiner

*Primary Examiner*—Nikita Wells
*Assistant Examiner*—Jennifer Yantomo
(74) *Attorney, Agent, or Firm*—Fulbright & Jaworski LLP

(57) ABSTRACT

Improved ion focusing for an ion mobility drift cell allows for improved throughput for subsequent detection such as mass detection. Improved focusing is realized by the use of alternating regions of high and low electric fields in the ion mobility drift cell.

50 Claims, 25 Drawing Sheets

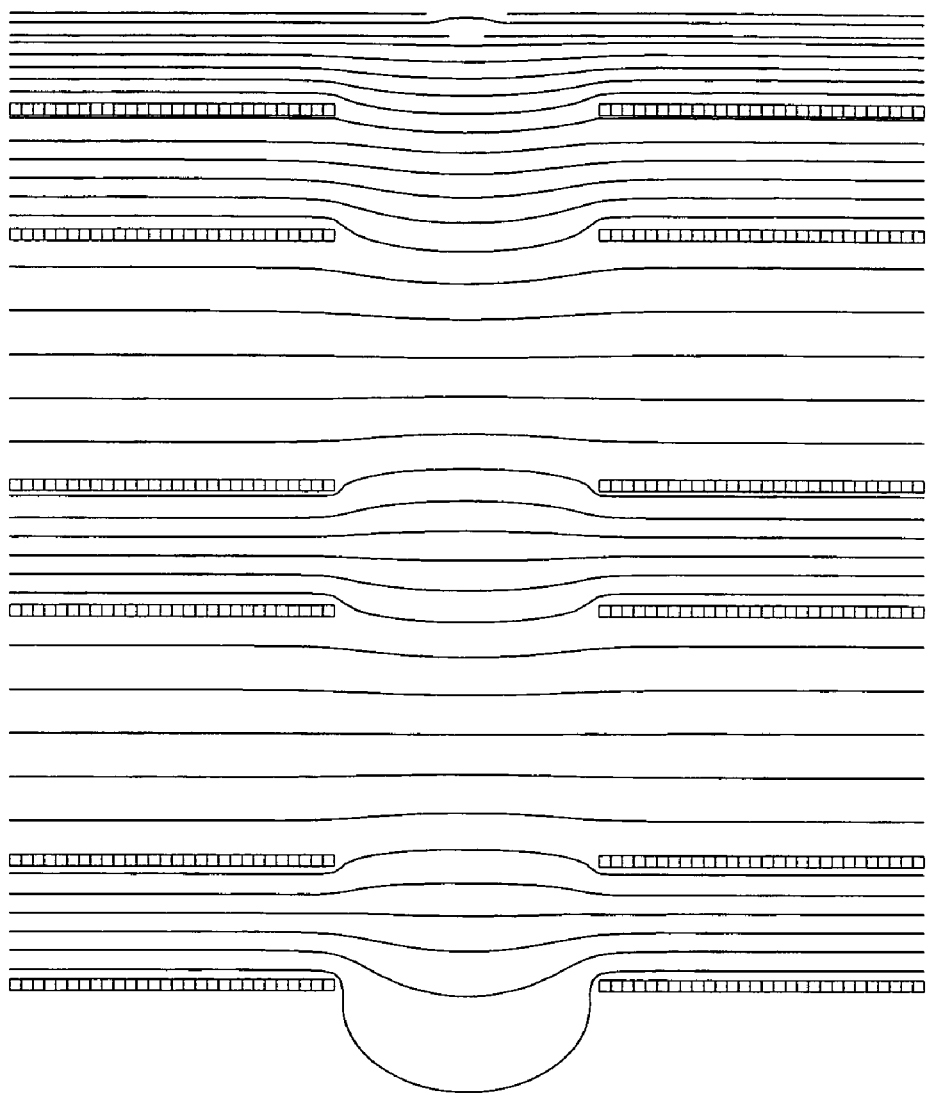
FIG. 2
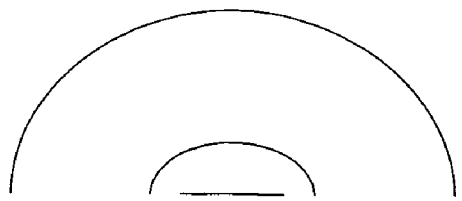

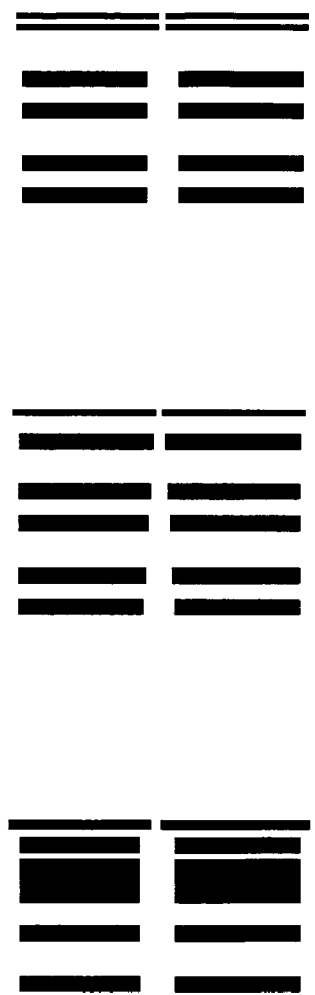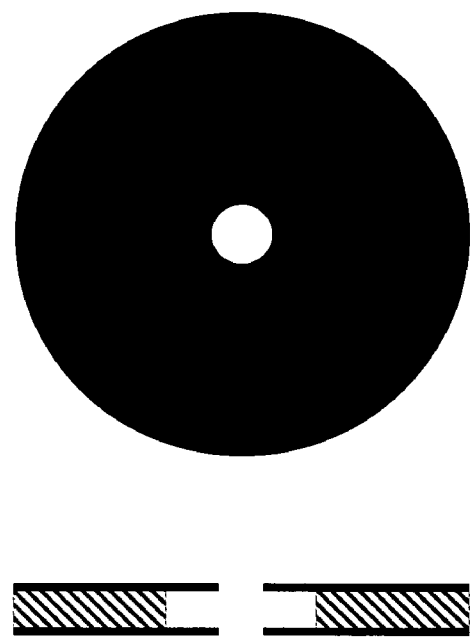

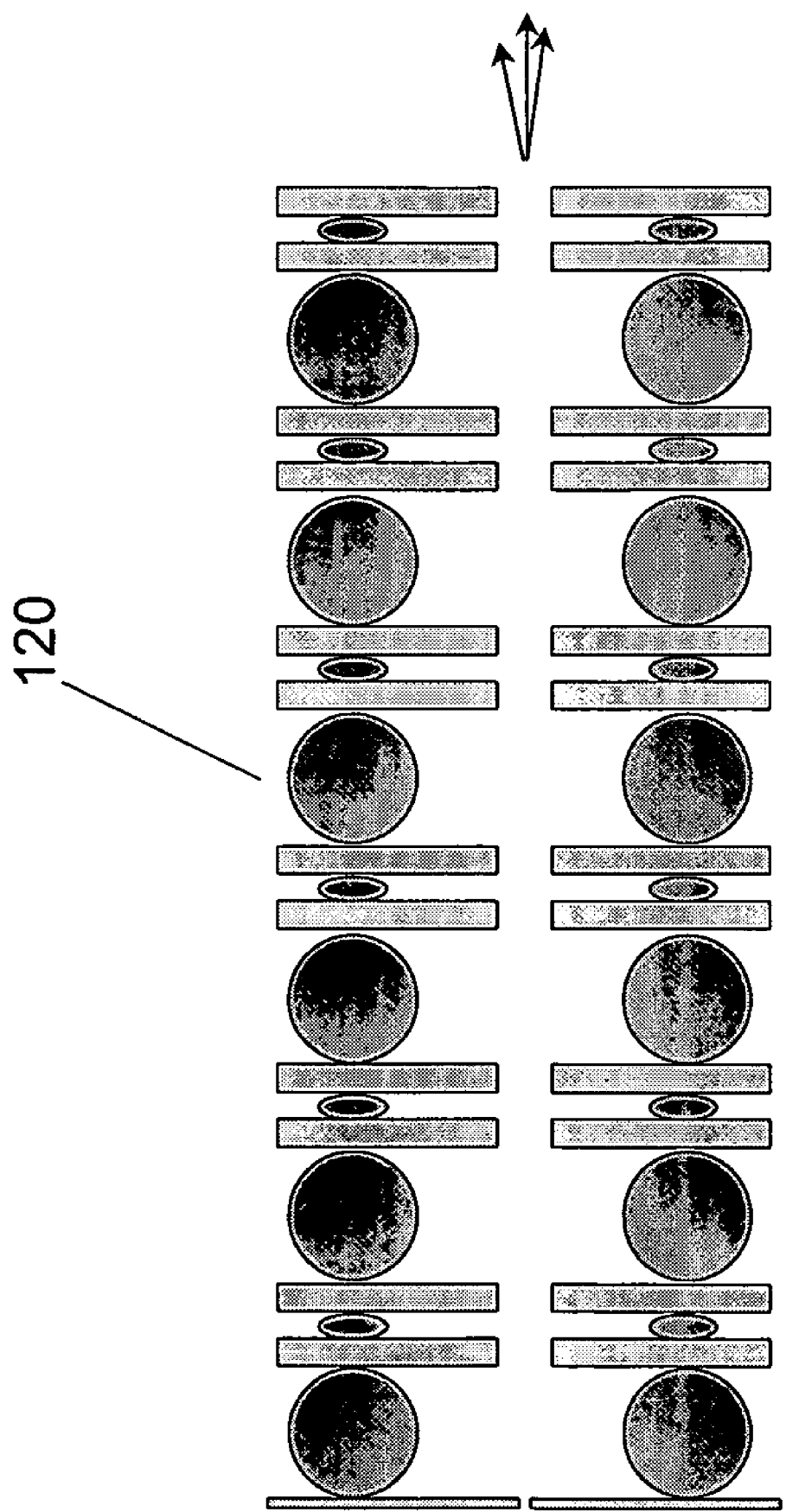

ION MOBILITY TOF/MALDI/MS USING DRIFT CELL ALTERNATING HIGH AND LOW ELECTRICAL FIELD REGIONS

CROSS-REFERENCE TO RELATED APPLICATION

This application claims priority to U.S. application Ser. No. 60/512,825, filed on Oct. 20, 2003.

STATEMENT REGARDING FEDERALLY SPONSORED RESEARCH OR DEVELOPMENT

This work has been funded in whole or in part with Federal funds from the National Institute on Drug Abuse, National Institutes of Health, Department of Health & Human Services under Contract No. N44DA-3-7727. The United States government may have certain rights in the invention.

TECHNICAL FIELD

The present invention relates generally to instrumentation and methodology for characterization of chemical samples based on improved ion mobility spectrometry (IMS). Specifically, the improvements lie in the area of ion focusing. The improved focusing may be used to improve throughput from an IMS instrument to a downstream instrument and method, preferably mass spectrometry (MS). The resulting instrument and method are useful for qualitative and/or quantitative chemical and biological analysis.

BACKGROUND OF THE INVENTION

An ion mobility spectrometer is typically composed of an ionization source, a drift cell, and an ion detector; examples of the latter include a sampling plate, an electron multiplier, or a mass spectrometer. Ion mobility spectrometry separates ions in terms of their mobility with reference to a drift/buffer gas measuring the equilibrium velocity which ions obtain. When gaseous ions in the presence of a drift gas experience a constant electric field, they accelerate until a collision occurs with a neutral molecule. This acceleration and collision sequence is repeated continuously. Over time, this scenario averages out over the macroscopic dimensions of the drift tube to a constant ion velocity based upon ion size, charge and drift gas pressure. The ratio of the velocity of a given ion to the magnitude of the electric field experienced by it is the ion mobility. In other words, the ion drift velocity ($v_d$) is proportional to the electric field strength (E) where the ion mobility $K=v_d/E$ is a function of the ion volume/charge ratio. Thus IMS is a technique similar to mass spectrometry, having a separation component to it. IMS is generally characterized as having high sensitivity with moderate separation power. Separation efficiency is compromised when "bands" of the various ions spread apart as opposed to remaining together in a tight, well-defined plug. Thus, the quality of the electric field maintained in the drift cell is critical to preserving and perhaps improving separation efficiency; i.e., resolution. It is also critical in applications where a downstream detection method is limited by ion throughput from the ion mobility drift cell. Improved focusing improves ion throughput to the downstream instrumental detection platform, thereby improving overall performance.

Prior art instruments employ various methods to obtain a linear electric field including utilizing: 1) a series of equally spaced rings connected through a resistor chain, 2) a tube coated with a resistive material in U.S. Pat. No. 4,390,784 to Browning et al., or 3) by a more complex method such as a printed circuit board assembly drift tube in U.S. Pat. No. 6,051,832 and PCT WO 98/08087 to Bradshaw. Von Helden (G. Von Helden, T Wyttenbach, M. T. Bowers Science 267 (1995) p1483) showed transport of MALDI ions desorbed from a surface and transported into a 1 Torr mobility cell and In 1995 Bristow showed the use of a MALDI matrix surface to generate ions inside an atmospheric ion mobility spectrometer (A. W. T. Bristow, C. S. Creaser, J. W. Stygall "Matrix Assisted Laser Desorption Ionisation-Ion Mobility Spectrometry, Abstract to Fourth International Workshop on Ion Mobility Spectrometry," Cambridge U.K. Aug. $6^{th}$–$9^{th}$ 1995).

The combination of an ion mobility spectrometer (IMS) with a mass spectrometer (MS) is well known in the art. In 1961, Barnes et al. were among the first to combine these two separation methods. Such instruments allow for separation and analysis of ions according to both their mobility and their mass, which is often referred to as two dimensional separation or two dimensional analysis. Young et al. realized that a time-of-flight mass spectrometer (TOFMS) is the most preferred mass spectrometer type to be used in such a combination because its ability to detect simultaneously and very rapidly (e.g. with a high scan rate) all masses emerging from the mobility spectrometer. Their combination of a mobility spectrometer with a TOFMS, in the following referred to as a Mobility-TOFMS. This prior art instrument comprised means for ion generation, a mobility drift cell, a TOFMS, and a small orifice for ion transmission from the mobility cell to the TOFMS.

Use of MS as a detector allows for resolution based on mass-to-charge ratio after separation based upon ion mobility. Shoff and Harden pioneered the use of Mobility-MS in a mode similar to tandem mass spectrometry (MS/MS). In this mode, the mobility spectrometer is used to isolate a parent ion and the mass spectrometer is used for the analysis of fragment ions (also called daughter ions) which are produced by fragmentation of the parent ions. In the following this specific technique of operating a Mobility-MS is referred to as Mobility/MS, or as Mobility/TOF if the mass spectrometer is a TOFMS-type instrument. Other prior art instruments and methods using sequential IMS/MS analysis have been described (see, e.g., McKnight, et al. Phys. Rev., 1967, 164, 62; Young, et al., J. Chem. Phys., 1970, 53, 4295; U.S. Pat. Nos. 5,905,258 and 6,323,482 of Clemmer et al.; PCT WO 00/08456 of Guevremont) but none combine the instrumental improvements disclosed presently. When coupled with the soft ionization techniques and the sensitivity improvements realizable through use of the drift cell systems herein disclosed, the IMS/MS systems and the corresponding analytical methods of the present invention offer analytical advantages: over the prior art, particularly for the analysis of macromolecular species, such as biomolecules.

The challenging issue when building a Mobility-MS is achieving a high ion transmission from the mobility region into the MS region of the tandem instrument. It is at this interface that the earlier goals of ion mobility technology of using a linear field appear incongruous with the goal of maximizing ion throughput across the IMS/MS interface. The mobility section is operating at a pressure of typically between 1 mTorr and 1000 Torr whereas the MS is typically operating at pressures bellow $10^{-4}$ Torr. In order to maintain this differential pressure it is necessary to restrict the cross section of the opening that permits the ions to transfer from the mobility section to the MS section. Typically this opening cross section is well below 1 mm$^2$. Hence it is desirable to focus the ions into a narrow spatial distribution before this transmission occurs.

As discussed above, in the early development of IMS, it was believed that the use of focusing methods (i.e., non-linear fields) was detrimental because it was believed that such focusing methods would deteriorate the resolution of the mobility spectrometer. Also, many of the early mobility spectrometers were used to investigate the mobility constant of ions, in which case it is preferable to use a homogeneous field of known value along the ion drift path. Therefore, most instruments simply used a large area ion detector at the end of the mobility drift and ion focusing was not an overarching concern. It was only when the need for compact and sensitive IMS emerged when the focusing of the drift ions was addressed.

In U.S. Pat. No. 4,855,595, Blanchard taught a focusing method based on time-varying electric fields. In 1992, Avida et al. U.S. Pat. No. 5,235,182 found that a slight inhomogeneous fringe fields along the mobility drift cell could be used to reduce the loss of ions from the edge of the mobility drift cell and hence to reduce the size of mobility instruments. The inhomogeneous fringe fields were generated by simply increasing the thickness of the field-generating ring electrodes such that the ratio of electrode thickness to inter-electrode gap could be manipulated to provide the fringe fields. The following year, Thekkadath (U.S. Pat. No. 5,189,301) taught a cup shaped electrode to generate a focusing field. This field configuration compares to the Vehnelt cylinder used in non-collisional ion optics. In 1996 Gillig et al. published a magnetic field to confine the ions in a small beam in order to increase the ion transmission from the mobility section into a mass spectrometer.

In 1999 Gillig used a periodic configuration of focusing and defocusing fields in order to increase the ion transmission from the mobility section into the MS section, as discussed above. This field configuration compares to a technique used in non-collisional ion optics where series of focusing and defocusing lenses are used to confine ion beams in large ion accelerators [Septier, p. 360]. Published U.S. application Ser. No. 2001/0032930 to Gillig et al. and U.S. application Ser. No. 2001/0032929 to Fuhrer et al. taught the use of a specific mobility cell electrode configuration to produce periodic and periodic/hyperbolic fields, respectively and superior focusing. U.S. Pat. No. 6,040,575 to Whitehouse et al., teaches surface charging of insulators to collect and slow down or selectively fragment the ions in the region of the orthogonal time-of-flight mass section.

Nonlinear electric fields have also been introduced to ion mobility drift cells to focus ions to a detector as presented in U.S. Pat. No. 5,189,301 to Thekkadath utilizing a cup electrode and U.S. Pat. No. 4,855,595 to Blanchard using nonlinear fields for the purpose of controlling ions, trapping ions in a potential well to normalize drift differences and increase sensitivity. All of these methods have drawbacks associated with their construction and ease of implementation. Therefore, it is the object of this invention to reduce or eliminate disadvantages and problems associated with prior art ion mobility instruments.

Copending U.S. application Ser. No. 09/798,030 to Fuhrer et al., filed Feb. 28, 2001 demonstrates that additional ion focusing in IMS is achieved by using a superposition of hyperbolic and periodic electric fields in a mobility cell.

Brittain, et al., in U.S. Pat. No. 5,633,497, describe the coating of the interior surfaces of an ion trap or ionization chamber with an inert, inorganic non-metallic insulator or semiconductor material for the passivation of such surfaces so as to minimize absorption, degradation or decomposition of a sample in contact with the surface.

Andrien, et al., in U.S. Pat. No. 6,600,155, describe the coating of a surface in the time-of-flight pulsing region with a dielectric film between other films, suggesting an improvement of ion beam properties before orthogonal extraction of ions into the drift region of a time-of-flight mass spectrometer.

Loboda, in U.S. Pat. No. 6,630,662 describes a method of enhancing performance of mobility separation of ions by balancing the ion drift motions accomplished by the influence of DC electric field and counter-flow of the gas. Using this balance of forces, ions are first accumulated inside the ion guide, preferably RF-ion guide, and then by changing of electric field or gas flow, gradually elute from the ion guide to some detector, preferably a TOF MS.

U.S. Pat. No. 6,707,037 to Whitehouse describes the proposed extraction of ions of both signs from a MALDI target directly located inside gas-filled RF-multi-pole ion guide with a concentration of ions along the separation axis and directing them in opposite directions under influence of axial electric field for further mass-analysis.

All of the U.S. patents, patent applications, publications referenced herein are incorporated by reference as though fully described herein.

Although much of the prior art resulted in improvements in focusing and therefore in ion throughput from the mobility cell to the mass spectrometer in tandem instruments, there is room for additional improvement in ion throughput. The inventors describe herein a mobility cell design which results in alternating regions of high and low electric field to provide improved ion focusing.

BRIEF SUMMARY OF THE INVENTION

The present invention makes clear the reason for focusing effect of such type of fields and enhances it, namely, by applying alternating high and low electric fields, and implements other advantages of this approach providing better mobility resolution and relatively simple implementation of collisionally-induced fragmentation of selected ions. The other suggestion mention in this, patent is using of microchannel plates for inserting of ions from mobility cell with relatively high gas pressure into low pressure region of mass-spectrometer. Such an approach can result in significant ion losses. To improve ion transmission through such micro-channel plates the faces and/or the interior surfaces of the microchannels are coated by thin dielectric film and various means of charging of this film by ions of the same sign as the desired analyte ions are herein now. A mulitpole radio frequency (RF) focusing and beam forming optic is proposed to create and transport ions emerging from a multichannel ion mobility cell wherein multiple ion sources are simultaneously or sequentially injected each into its own individual channel. The action of the RF multipole optic is to maintain the physical separation of the individual mobility separated ions from each multichannel and to create and maintain a substantially parallel array of beamlets (which are themselves substantially parallel trajectories of ions emerging from each mobility channel) between the exit of the mobility cell- and the entrance to the extractor region of a TOFMS. The RF focusing and transport optic may be located before or after a differentially pumped gas skimmer region or may have gas skimmer regions incorporated into its optical design.

A number of embodiments are described herein. It should be clear that other combinations of embodiments not expressly recited herein, but known to one of skill in the art upon a reading of this description, are within the scope of the present invention.

The present invention is directed to a system and method relating to ion mobility drift cells transporting ions in a gas at high pressures. Ions entering such a drift cell travel to the end of the cell under the effect of an electrical field. Differences in molecular shape allow separation of ions according to their ion mobility drift time. This cell can also be applied as a pre-separation stage prior to a time-of-flight mass spectrometer (TOF) for the analysis of complex mixtures of chemical and/or biological substances. This cell allows for cooling the entering ions and transmitting a large fraction of them. Ion losses through decomposition or discharging of electrodes are limited by using special geometry of electrodes and alternating strong and weak field regions within the cell. The application of high field is carefully applied over a distance which is less than the mean free path of the gas within the ion mobility cell. This principle allows the application of several hundred volts/mm before gas discharge occurs. Such high voltages can be used to continually refocus the ions as they periodically pass through the strong field regions. High mobility resolution is nevertheless maintained because the ion trajectories are always randomized after each refocusing so that the distance traveled by each ion over the dimensions of the mobility cell averages to nearly the same distance. Also, the application of higher voltage between selected electrodes in the cell can provide spatially localized collision induced dissociation of ions and their fragments for the efficient structural identification (sequencing) of complex biological analytes. When higher voltages are desirably applied to intentionally create a discharge, the discharge dose not propagate along the length of the cell because it is nicely localized by the low field regions on either side.

In one aspect of the present invention there is an apparatus comprising an ion source, a first ion mobility drift cell, said first ion mobility drift cell having an entrance fluidly coupled to the ion source, said first ion mobility drift cell comprising at least two electrode pairs having an intra-electrode gap between individual electrodes of a pair which is smaller than an inter-electrode gap between electrode pairs, and an exit. In one embodiment, the electrodes near the exit of the ion mobility cell have greater thickness than electrodes further removed from the exit of the ion mobility cell. In one embodiment, the electrodes near the exit of the ion mobility cell are of smaller diameter than electrodes further removed from the exit of the ion mobility cell. In one embodiment of the apparatus, the electrodes near the exit of the ion mobility drift cell have an aperture comparable in dimension to the dimensions of the exit. In one embodiment, one or more electrode pairs near the entrance of the ion mobility cell have smaller outside diameter than one or more electrode pairs farther away from the entrance. In one embodiment, the first several sets of electrodes near the entrance of the ion mobility cell have an increasing outside diameter. In one embodiment, the apparatus further comprising an RF (radio frequency) voltage and a dc (direct current) electrode voltage, wherein said RF voltage is superimposed on said dc electrode voltage. In one embodiment, the apparatus further comprises a time-of-flight mass spectrometer fluidly coupled to the exit of the mobility drift cell by way of an orthogonal extractor and a low energy monochromatized electron beam coupled to said orthogonal extractor. In one embodiment of the apparatus, the exit comprises a plurality of apertures. In one embodiment, the plurality of apertures is comprised of a 4033 circular array of apertures, the array having a diameter of 5.37 mm and a total aperture area of 8 $mm^2$. In one embodiment, one or more electrodes in the drift cell has a plurality of apertures. In one embodiment, the distribution of apertures in the electrode pairs changes from the entrance to the exit. In one embodiment, the distribution of apertures changes from a circular distribution to a horizontal rectangle distribution. In one embodiment, the exit is at least partially coated with a thin insulating film. In one embodiment, the insulating film comprises piezoelectric film. In one embodiment, the apparatus further comprises structures comprising piezoelectric thin films at one or more locations within the mobility drift cell. In one embodiment, the first mobility drift cell one or more collision induced dissociation regions within it. In one embodiment, the collision induced dissociation region is placed near the exit of the mobility drift cell. In one embodiment, the collision induced dissociation region is placed near the center of the mobility drift cell. In one embodiment, the ion mobility drift cell further comprises at least one porous semiconductor electrode. In one embodiment, the porous semiconductor electrode is located directly after the entrance. In one embodiment, the at least one porous semiconductor electrode is coated with a dielectric or piezoelectric thin film. In one embodiment, the ion source is a MALDI source. In one embodiment, the ion source is a secondary ion source. In one embodiment, one or more of the electrode pairs are replaced with electrodes triads. In one embodiment, at least one of the electrodes is a multiaperture conical skimmer electrode. In one embodiment, the apparatus further comprises a differentially pumped interface fluidly coupled to said ion mobility drift cell; a conical skimmer fluidly coupled to said differentially pumped interface; an extractor fluidly coupled to said conical skimmer; and, a time-of-flight mass spectrometer fluidly coupled to said extractor. In one embodiment, the apparatus further comprises a differentially pumped interface fluidly coupled to said ion mobility drift cell; a multihole skimmer fluidly coupled to said differentially pumped interface; an extractor fluidly coupled to said multihole skimmer; and, a time-of-flight mass spectrometer fluidly coupled to said extractor. In one embodiment, said ion mobility drift cell forms part of a multibore ion mobility spectrometer. In one embodiment, at least one of said electrode pairs is comprised of flexible copper-kapton-copper material. In one embodiment, the apparatus further comprises a multichannel RF interface fluidly coupled to said drift cell; an extractor fluidly coupled to said multichannel RF interface; and a time-of flight mass spectrometer fluidly coupled to said extractor. In one embodiment, the apparatus further comprises an second ion mobility drift cell fluidly coupled to said first ion mobility drift cell, said second ion mobility drift cell comprising electrode pairs having an intra-electrode, gap which is smaller than an inter-electrode gap between electrode pairs; and, a differentially pumped interface fluidly coupled to said second ion mobility drift cell. In another embodiment, the apparatus further comprises a conical skimmer fluidly coupled to said differentially pumped interface; an extractor fluidly coupled to said conical skimmer; and, a time-of-flight mass spectrometer fluidly coupled to said extractor. In another embodiment, one or more of said electrode pairs of said first ion mobility drift cell, said second ion mobility drift cell, or both, are replaced with electrodes triads.

In another embodiment, there is an apparatus comprising a source of ion or neutral species, a first and second ion mobility drift cell, said first and second ion mobility drift cells being substantially horizontally opposed to one another and fluidly coupled to said source, wherein one or both of said ion mobility drift cells comprise at least two electrode pairs having an intra-electrode gap between individual electrodes of a pair which is smaller than an inter-electrode gap between electrode pairs, and, a first mass spectrometer fluidly coupled to said first ion mobility drift cell and a second mass spectrometer fluidly coupled to said second ion mobility drift cell. In another embodiment, the apparatus further comprises a fragmentation source positioned to fragment ions and neutral species entering one or both of said first and second ion mobility drift cells. In another embodiment, the first mass spectrometer, the second mass spectrometer, or both, are time-of-flight mass spectrometers.

In another aspect of the present invention, there is a method of analyzing ions according to their mobility in a gas comprising a first ionization step to form ions from an analytical sample, introducing said ions into a mobility drift cell, applying regions of alternating high and low electric field along the separation axis of the drift cell, and detecting the ions. In one embodiment, the method further comprises the step of applying an RF voltage superimposed on a dc electrode voltage along at least a part of said separation axis. In one embodiment, the method further comprises the step of changing the charge of ions after said step of applying. In one embodiment, the step of detecting comprises detecting with a mass spectrometer. In one embodiment, the mass spectrometer is a time-of-flight mass spectrometer. In one embodiment, the method further comprises the step of RF focusing of said ions before said step of detecting with a time-of-flight mass spectrometer. In one embodiment, the step of said first ionization comprises forming ions using a MALDI ion source. In one embodiment, the step of said first ionization comprises forming ions using a secondary ion source. In one embodiment, the step of said first ionization comprises forming ions using a electrospray ionization combined with an ion trap. In one embodiment, the method further comprises a second ionization step. In one embodiment, the step of applying regions of alternating high and low electric field comprises applying two substantially horizontally opposed regions of alternating high and low electric field through the use of two substantially horizontally opposed ion mobility drift cells. In one embodiment, the step of detecting comprises detecting with a mass spectrometer. In one embodiment, the said step of detecting with a mass spectrometer comprises detecting with a time-of-flight mass spectrometer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 2. Illustration of field lines in a short typical cell with three electrode pairs simulated by SIMION.

FIG. 3. Schematic illustration of exemplary electrode configurations at the end of the mobility cell, 3A: thicker electrodes near the cell exit; 3B: electrodes of decreasing opening diameter; 3C: electrodes with very narrow gap and small opening; 3D: electrode doublet produced by bonding metal discs to ceramic and laser cutting aligned holes; 3E: circular aperture.

DETAILED DESCRIPTION OF THE INVENTION

Figure 1:
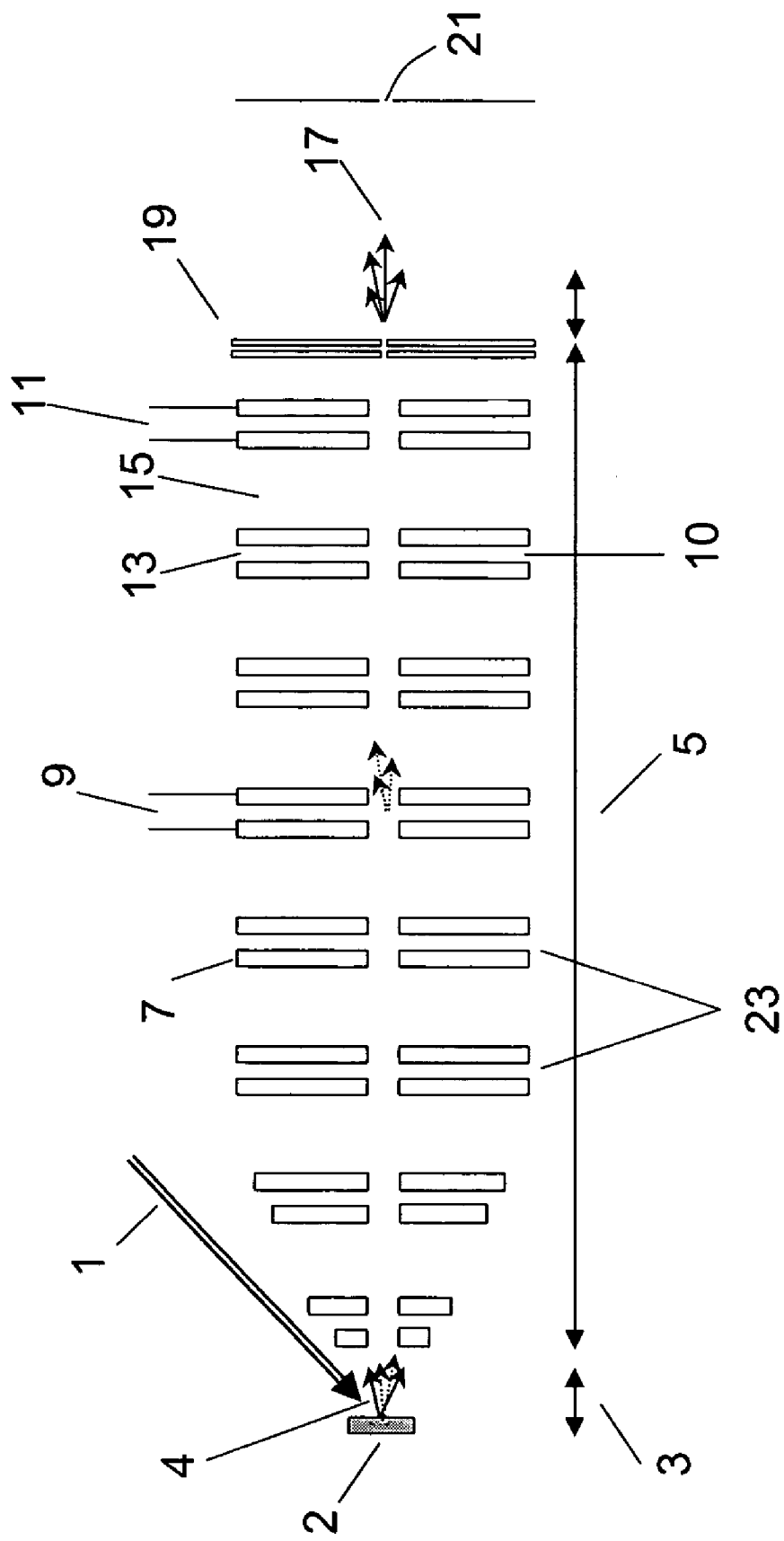
FIG. 1. Schematic of an ion mobility drift cell with alternating high and low electrical field regions.

As used herein, "a" or "an" means one or more. Unless otherwise indicated, the singular contains the plural and the plural contains the singular.

As used herein, "aperture" means "hole" or "orifice".

As used herein, an "electrode triad" is a distinct group or cluster of three electrodes.

As used herein, the term "intra-electrode gap" refers to the gap between two electrodes of an electrode pair.

As used herein, the term, "inter-electrode gap" refers to the gap between electrode pairs.

As used herein, "MALDI" means matrix assisted laser desorption ionization.

As used herein, "SIMS" means secondary ion mass spectrometry.

As used herein, the term "TOF" is defined as a time-of-flight mass spectrometer; as used herein, "oTOF" is defined as a time-of-flight mass spectrometer configured orthogonally to the analytical axis of a preceding instrumental platform such as, for example, the separation axis of an ion mobility cell.

As used herein IM-oTOFMS refers to a combination of an ion mobility spectrometer with an orthogonal time of flight mass spectrometer.

Electrode Configurations for Ion Focusing

In applications where ion mobility cells filled with a few Torr of buffer gas are used as a volume/charge separation stage in front of a mass spectrometer, the cooled ions exit through a small aperture into a differentially pumped low pressure region within the mass spectrometer. To minimize transmission losses within the ion mobility cell at the exit orifice, the ion beam inside the drift cell has to be focused.

In the new design of the present invention, alternating regions of high and low field are used to provide the focusing (FIG. 1) along the entire mobility cell which is filled with gas at a pressure of between 1 and several hundred Torr. Most commonly this gas will be helium, although other gases or gas mixtures may be used. The alternating high and low field regions are created by varying the distance between electrodes, while the bias voltage between all electrodes is the same. Alternatively, the small gaps (7) and the large gaps (15) between electrode pairs may be biased by independent power supplies to any desired ratio limited only by the onset of electrical discharge through the gas along the central axis of the mobility cell. The width of the small gap (7) is chosen so that it is comparable or less, preferably substantially less, than the mean free path of electron motion in the gas at a particular operating pressure. By so doing, high voltages in these gaps can be applied without causing an electrical discharge along the axis of the mobility cell. A pulsed laser or particle beam or other ionizing radiation (1) is used to desorb ions and neutrals from a surface (2) (which may be a MALDI matrix preparations) so that ions and neutrals are injected into the initial ion transport region (3). The ions may be derived from a MALDI or SIMS desorption process, among others. Desorbed ions then rapidly (within a few hundreds of nanoseconds) enter the ion mobility drift cell (5). In the meantime, the neutrals which were desorbed from the surface (2) are cooled and then transported more slowly by the mobility carrier gas flow through the initial transport region (3). A neutral post desorption ionization source (4) which is most commonly an energetic photon source which may be a laser is timed to intersect these cooled neutrals as they migrate away from the surface (2). The post ionized neutrals will then enter the mobility cell (5) some several microseconds after the directly desorbed ions. High field regions are created between the sets of two very closely spaced electrodes rings ("paired" electrodes), one of which is illustrated by (7). Also, several of the small gaps, for example (9) and (11) can be configured so that additional voltage pulses can be applied to achieve collision-induced dissociation of mobility separated ions within these gaps. These gaps are configured with at least two electrodes to which a momentary voltage pulse is applied sufficient to produce a collision induced dissociation of a particular mobility separated ion which has just entered this region of the mobility cell. Dissociation of mobility separated ions can also be achieved by impinging ionizing radiation (10) at a specified time during which a mobility separated ion enters an intra-electrode gap (13). This ionizing radiation may be a laser which is focused through a transparent window into the intra-electrode gap (13). The gap (13) between individual electrodes in an electrode pair is a high field region, while the gap (15) between electrode pairs (23) is a low field region. Field penetration from the narrow gap between electrodes into the large gap provides a component of electric field in the direction perpendicular to the axis, which leads to the focusing of ions. Cooled ions (17) exit the mobility drift cell (5) after passing the final electrode pair, i.e., the exit pair (19). The ions then proceed to the mass spectrometer entrance (21).

An example of this field penetration for different inter-electrode spacings is shown in FIG. 2 (a SIMION simulation). The relevant parameters are as follows. The entrance field is 100 V/cm. The distance between the target and first electrode is 5 mm. The thickness of the electrodes is 200 $\mu$m and the opening diameter 2.2 mm. The intra-pair gap is 1.6 mm and inter-pair gap 4 mm. 100 V is applied between each electrode, creating fields of 625 V/cm inside a pair and 250 V/cm between pairs. Field penetration can be seen in front of the entrance region which focuses the ions toward the cell separation axis. The exit pair is also shown: the electrodes are thinner (100 $\mu$m) and only 100 $\mu$m apart. The gap between this exit pair and the precedent pair is also smaller (0.5 mm). 100 V is also applied between the exit and precedent pairs (200 V/cm) and inside the exit pair electrodes (10 kV/cm). As shown by the field lines, the exit electrode pair prevents the defocusing at its entrance. The beam is further focused to enter the low pressure analyzer region through the 300 $\mu$m aperture. The equipotential electric field lines help to visualize the focusing field effect. Inside the small gaps there is an opposite component that tends to defocus ions, but the field is stronger, and, therefore, the ions move much faster and spend less time in this region compared to the large gaps. The net effect consists in preventing ions from being lost on the electrodes and in their concentration close to the cell axis, and finally, their transmission through the skimmer orifice.

Additional focusing of ions into the orifice can be achieved by a special configuration of a few last electrodes. In one embodiment, the thicker electrodes can be used at the end of the cell (FIG. 3A). In another embodiment, decreasing diameter of electrodes is used (FIG. 3B). Finally, it is possible to use a pair of electrodes with a very narrow gap and small opening comparable with the exit orifice (FIGS. 2 and 3C). The "opening" is the space between the upper and lower electrodes and should be distinguished from both the inter- and intra-electrode gaps. Strong field penetration from this gap is likely to provide good focusing of the ion beam into the mass spectrometer.

A way to produce such doublet electrodes is shown in FIG. 3D. These doublets can be made by bonding metal discs to ceramic and laser cutting aligned holes in both pieces of metal. Alternatively the discs can be made out of polyimide which is metalized on both sides. Typical dimensions of the hole size might be 0.5 mm and the spacing of the doublet is also 0.5 mm. FIG. 3E is a front view of the doublet electrode of FIG. 3D. Thus, approximately three times the number of these doublets in the same linear distance as shown in the SIMION simulation of FIG. 2 could be used. It is possible to raise the voltage several times higher as compared to the more widely spaced geometry of the larger gapped structures shown in FIGS. 1 and 2 without increasing the fragmentation of the molecular ions.

The distance between two adjacent electrodes should be smaller or comparable to the mean free path of electrons at the cell gas pressure in order to prevent the development of the electron avalanche and the glow discharge in the high field region. The risk of starting a discharge through the channel will be eliminated since high energy electrons formed inside the high field region are slowed down in the low field regions and are unlikely to propagate the discharge. Low field regions are created between the paired electrodes by positioning the paired electrodes so that there is a significantly larger space between each pair (inter-electrode gap) than that between the electrode elements of each pair (intra-electrode gap).

With the alternation of low and high fields, it is possible to use a much higher overall voltage bias along the cell without incurring gas discharge, compared to a cell having equally spaced electrodes. The higher average field will result in higher average drift velocity of ions and better mobility resolving power in a shorter overall geometry. Overall ion transmission and resolution will be improved as the ion trajectories will be continuously refocused closely along the axis of the tube.

The use of narrower gaps in the instrument of FIG. 1 accomplishes several things. For example, the field strength which can be applied without breakdown at higher pressures increases. The mean free path of the gas becomes shorter as the pressure increases and collisions become more frequent. Accordingly, the small gap width must be matched to be about of the mean free path for electron-atom collision or breakdown will occur at a lower voltage than that desired. As a result, the hole sizes must also decrease so that the field penetration from the narrow gap between electrodes into the large gap (as shown in FIG. 2) can be contained to a region not much larger than the hole diameter. This prevents discharge, but still allows some field penetration so that the ions traversing the large (low field) gap will experience a focusing field as they approach the first electrode of the high field small gap doublet (electrode pair).

As is also shown in FIG. 1, additional measures may be taken to prevent ion losses in the region between the source and the entrance of the mobility cell. The first several sets of electrodes have a small but increasing outside diameter so that it is possible to position the entrance of the cell very close to the sample (about 4 mm) and still allow for the laser or ion beam to be incident at a steep angle necessary to obtain good focusing. This small physical profile of the mobility cell is especially useful in applications where a miniaturized approach to the mobility and/or mass spectrometry is required. One such important example is in the case of a Laser Desorption Microscope (such as the well-known LAMMA design) which may be substantially improved if the mass spectrometer minimally interferes with the coaxial axis of the Schwarzschild optics which focus the laser onto a submicron area of the surface. The advantages of this design have been demonstrated both experimentally and by simulations. Additionally, an RF voltage can be superimposed on the dc electrode voltage to enhance the ion focusing.

High Voltage Biasing of the Cell

Another advantage of these structures has to do with improving the performance of orthogonal MALDI or electrospray mass spectral analysis. In state of the art orthogonal MALDI for example, the ions are desorbed into several tens of mTorr pressure and cooled with quadrupoles which are operated near electrical ground reference. The cooled ions are then injected into the orthogonal extraction plates in an orthogonal time-of-flight mass spectrometer (OTOF) where they are given up to a few kilovolts of energy from the high voltage pulse applied to the extractor plates. The ions then disperse in either a linear or reflector time of flight section. They are given their final high kinetic energy by an attractive electrical potential which is applied to the front of the detector. This potential is maintained at as high an attractive electrical potential as possible to give the ions maximum acceleration energy to enable the best possible detection of large biomolecular ions. This high electrical potential requires that the output of the detector be either optically or electrically decoupled from the amplification and timing circuitry which is operated at ground. This decoupling limits the high voltage applied to the front of the detector to around 10–20 keV or less.

In contrast, the instant mobility cell will allow the MALDI ions to be formed near ground potential and then they can climb (or descend) within the mobility cell to high voltages such as −10 keV before they enter the mass spectrometer. The mass spectrometer must then be floated to this high potential; however, if the sign of the charge of the bio-ion can be changed in the orthogonal extraction region of the time-of-flight mass spectrometer (TOF) from positive to negative, the ion detector in the TOF can be operated with its output at ground. Changing the charge may be accomplished by a low energy monochromatized electron beam tuned to electron attachment resonances of the ion and subsequent neutral species after the attachment of two electrons. This electron beam can alternatively be used to fragment the ions within the orthogonal extraction region into positive and negative fragments which can then be accelerated into the mass spectrometer using appropriate biasing. Alternatively, the charge may be changed by chemical ionization reactions which would change the charge from positive to negative while the ions are in the region between the orthogonal plates. Alternatively, the charge can be altered by photo-affinity labeling the analyte with some negative ion adduct or electron attachment reactions. The detector does not have to be operated at ground potential but can be biased to between 10–20 keV so that the kinetic energy of the large bio-ions would for example approach 30 keV upon reaching the detector. This charge conversion in the orthogonal plates not only improves the detection efficiency, but it also may improve specificity and reduce clutter by ionizing only certain types of molecules which have electronegative groups such as sulfhydrils or phosphate. Another well known example is the energy specific. (resonant) attachment of electrons to small molecules such as explosives which contain nitro groups or larger biomolecular ions. The ability of the instant mobility cell to withstand high voltages without causing gas discharge makes it easier to time voltage sequences so that the entire electrical potential of the IMS and TOF spectrometers can be raised or lowered linearly or non-linearly during the time that the desorbed ions are inside the mobility cell. In this way the electrical potential of the ions exiting the mobility cell will be increased relative to the electrical potential of the ion detector in the TOF. This facilitates detection larger and larger ions such as for example proteins.

Concept of Multi-apertures

Figure 4C:
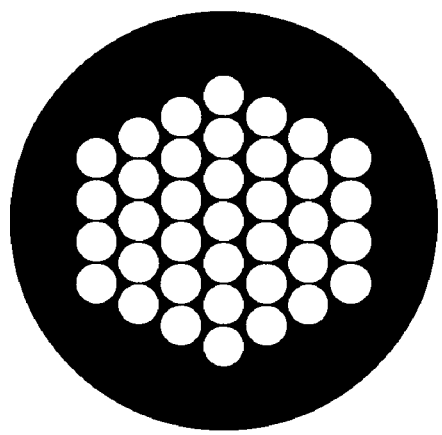
FIG. 4. Comparison of a single-hole aperture and multi-hole aperture; 4A: single aperture; 4B: cross sectional view of 4A; 4C multi-aperture; 4D cross sectional view of 4C.
Figure 4D:
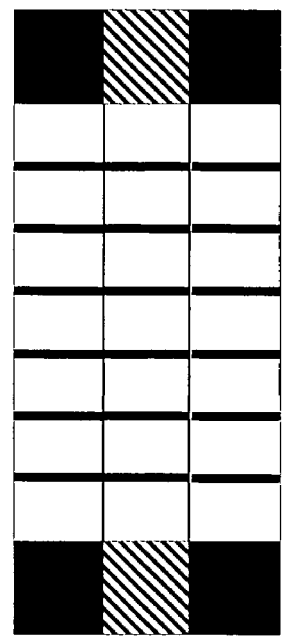
Figure 4A:
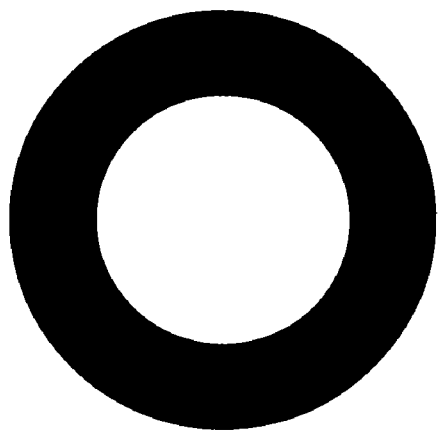
Figure 4B:
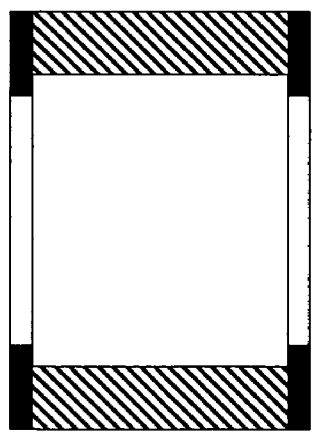
Figure 5:
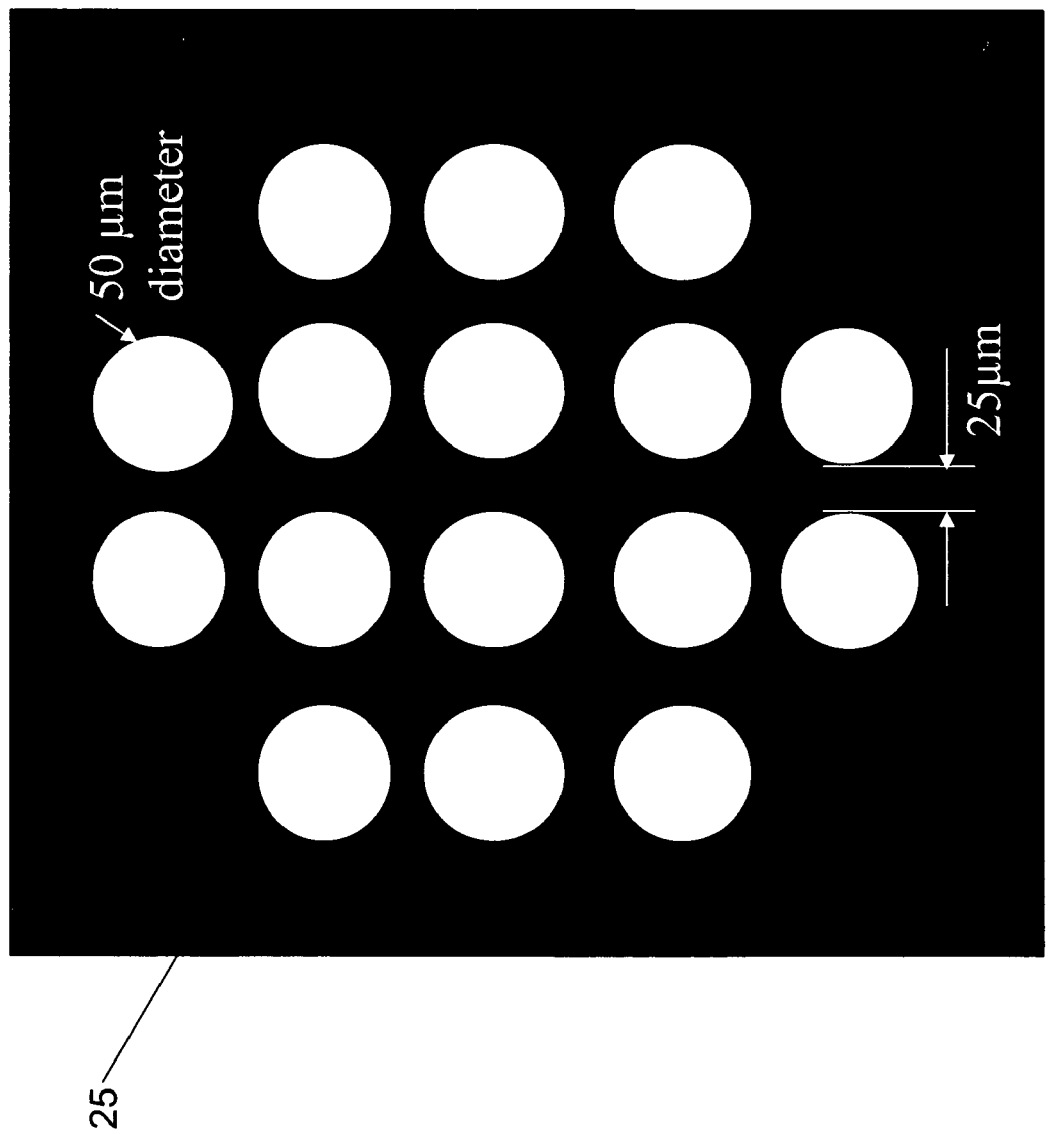
FIG. 5. Schematic illustration of a circular array of 50 $\mu$m diameter holes spaced by 25 $\mu$m.

The use of a multi-hole aperture instead of a single-hole aperture having a similar total open area improves the transmission and differential pumping from the mobility cell to the high vacuum region of the mass spectrometer. FIGS. 4A–D illustrate the general concept of using multi-hole apertures versus a single hole aperture. FIG. 4A shows a single aperture and FIG. 4B demonstrates the cross sectional view. FIG. 4C shows a multi-aperture exit and FIG. 4D shows the corresponding cross sectional view FIG. 5 shows an example of an arrangement of holes in a circular array comprising a web area (25). Such a circular array will ideally have about 4033 holes and will be used to replace the 1/8 inch diameter *single-hole aperture*. The same opening area of 8 mm² will be covered by a 4033 holes-circular array of 5.37 mm diameter. The holes are 50 μm diameter spaced by 25 μm. The 1/8 inch single hole aperture is replaced by a 4033 holes-circular array of 5.37 mm diameter; both having the same opening area of 8 mm². The 300 μm exit aperture will be replaced by an aperture with 36 50 μm-holes distributed on an array of 508 μm diameter. While specific examples in terms of dimensions have been disclosed above, it is understood by those of skill in the art that other variations in the multi-aperture embodiment are within the scope of the invention.

Figure 6A:
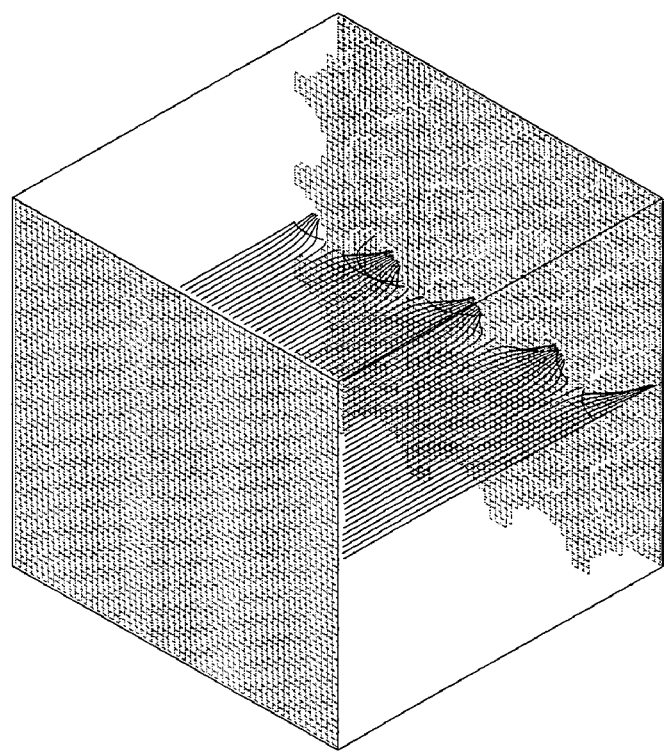
FIG. 6. SIMION simulations showing the focusing effect of the multi-hole aperture, 6A; and the resulting equipotential electric field lines, 6B. 6C shows a cross-section of the SIMION simulation of the configuration which has an addition of a third biasable element made up of electrically connected small cones.
Figure 6B:
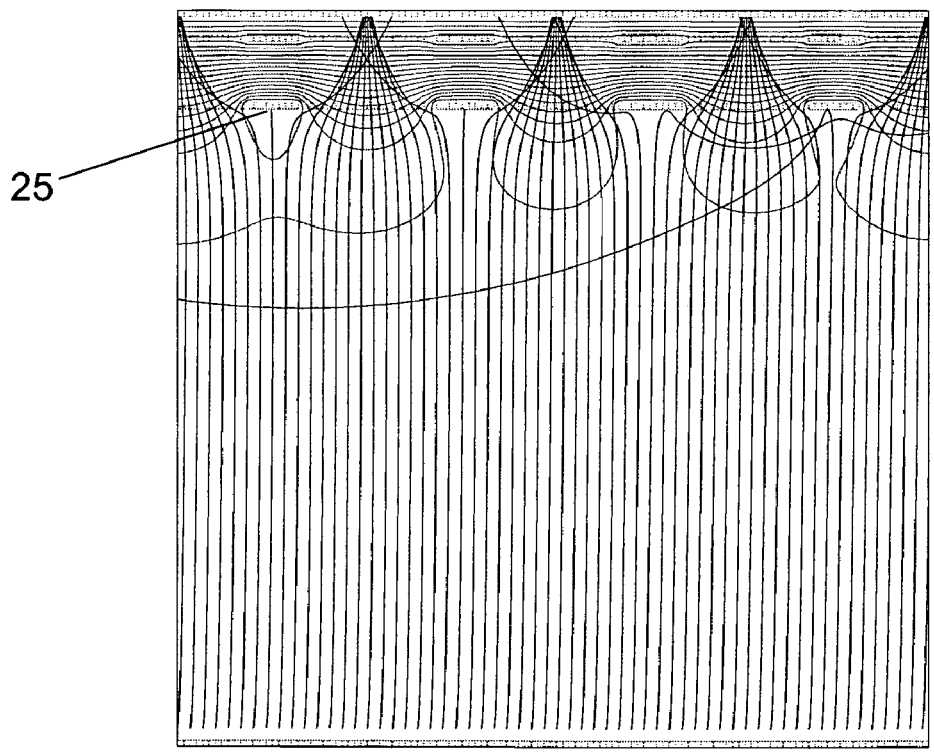
Figure 6C:
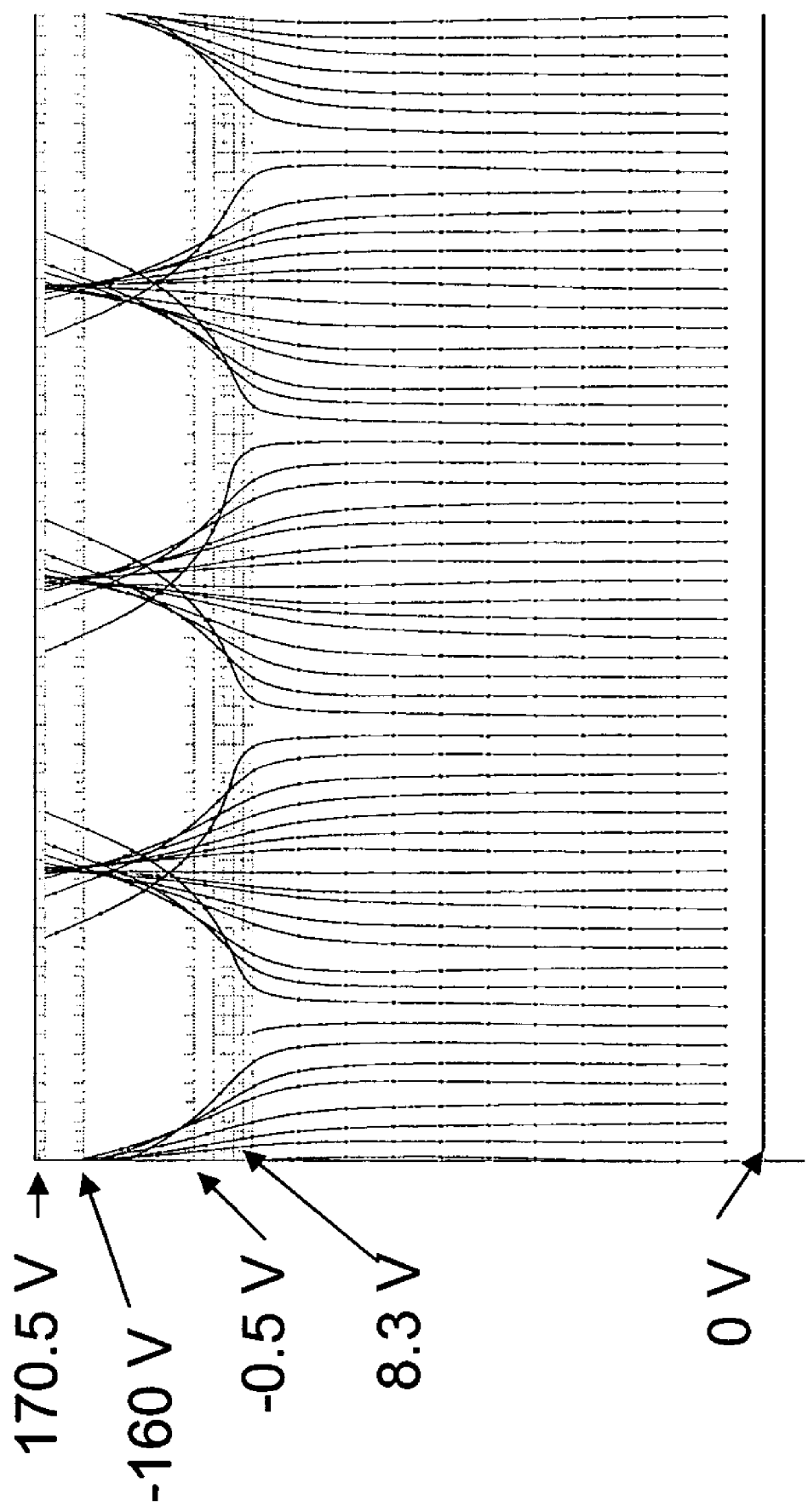

As shown by the SIMION simulations (FIG. 6), the field created between a pair of multi-hole apertures separated by 25 μm focuses the cooled ions. As the diameter of the array of holes is larger than the single-hole diameter, the array "intersects" with a larger part of the cooled ion beam than a single hole-aperture. With the focusing effect of the holes, the transmission is enhanced. The multi-hole aperture also reduces the space charging. Since the mean free path of the mobility gas (about 1 mm in 1 Torr He) is larger than the hole diameter, the multi-hole aperture likely intercepts more molecules than a single-hole aperture having the same opening area. In other words, the multi-hole aperture helps differential pumping. The transmission will be significantly enhanced by the use of a multi-hole aperture instead of single-hole aperture. The field penetration between holes focuses the ions. In this simulation (in vacuum), the electrodes are 5 μm thick, the insulating material (e.g. polyimide) is 25 μm thick. The cooled ions have initial energy in the mV range and are accelerated by 500 mV in front of the first multi-hole aperture. Between the two multi-hole apertures, a field of 24 V/mm is applied. FIG. 6C shows a cross-section of the SIMION simulation which tracks ions into a multiaperture paired exit electrode to which a third biasable electrode has been added. This third electrode is situated above the web area (25) which is the solid electrode material and insulator remaining on the face of the aperture between the open holes. By so positioning the biasable electrode, almost all ions approaching this web area are deflected by the combined effects of the field penetration and the gas flow into one or the several open holes bordering the specific portion of the web which the mobility ion has approached. It is understood also that a fourth such electrode could be added to the back side of the multiaperture paired electrode. The electrodes may not need to be biasable, but could comprise a thin dielectric coating which would charge to produce a dipole field repulsion of the mobility ions as they approached the web area (25). Alternatively, the electrode could comprise a piezoelectric thin film (which may also be coated with a thin dielectric) which could be biased to produce this dipole field.

Figure 7A:
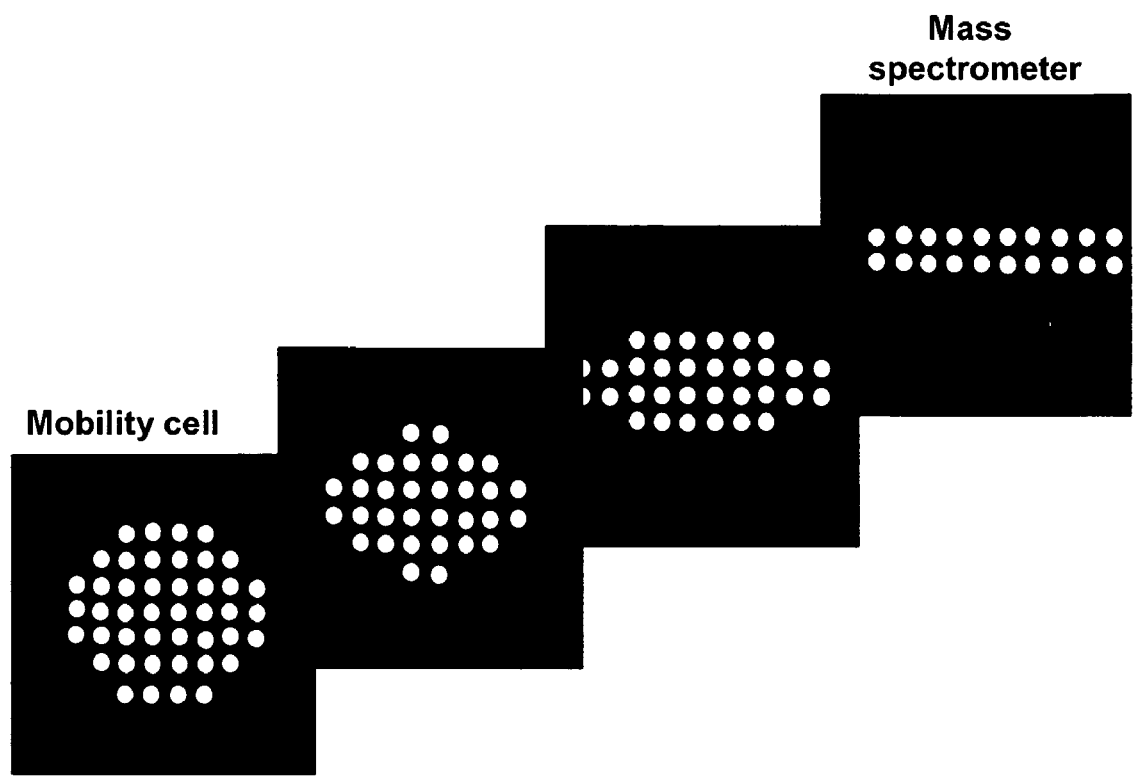
FIG. 7. Schematics showing progressive change of the distribution of the holes to change the beam profile from a circular spot to a narrow horizontal rectangle; 7A, front view; 7B, cross-sectional view.
Figure 7B:
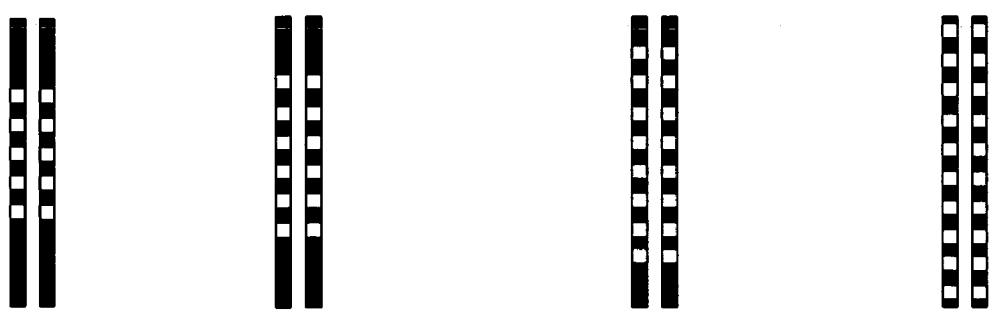
Figure 8A:
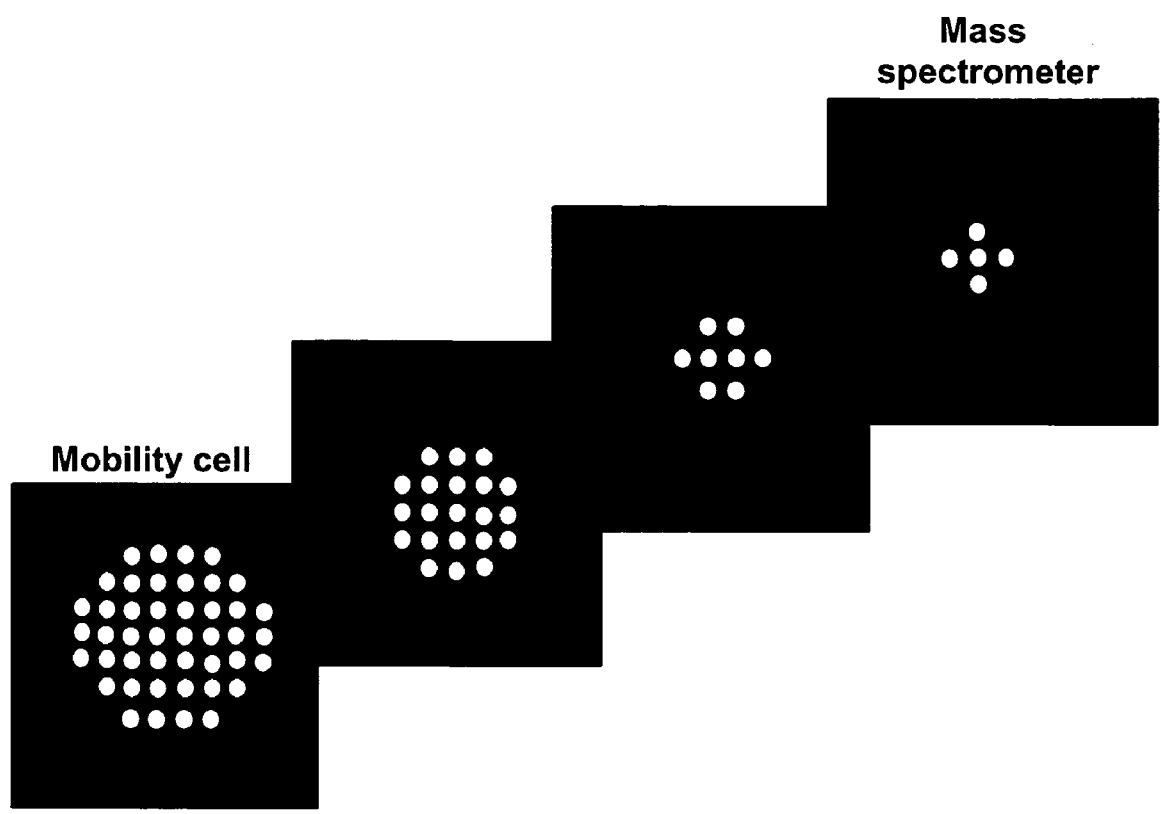
FIG. 8. Schematic showing reduction of the ion beam size from 8 mm$^2$ open area multi-hole aperture (corresponding to the usual ⅛ inch diameter-opening) to the 0.07 mm$^2$ multi hole-aperture (corresponding to the usual 300 $\mu$m diameter-opening); 8A, front view; 8B, cross-sectional view.
Figure 8B:
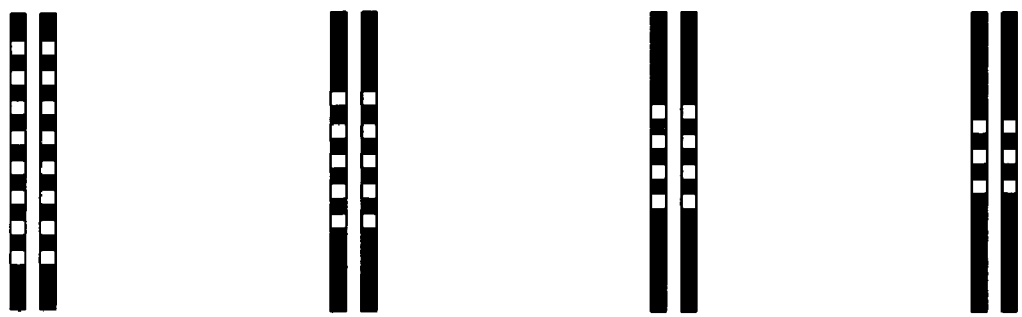

The use of these multiaperture paired electrodes is not restricted exclusively to improving the performance of the exit aperture—particularly if the third and fourth electrodes shown in FIG. 6C are added to reduce or eliminate any loss of mobility ions on the web area (25). It is then possible to use these multiaperture paired electrodes as the electrodes for the mobility cell region (5) itself. If the size of the array is gradually reduced as the ions are transported toward the cell exit (keeping the size of the hole and their arrangement the same), the focusing effect of the multiaperture paired structure can then be used to optimize the transmission. FIG. 8 schematically shows such a usage (the figure is not drawn to scale and shows doublet electrodes only although it is understood that triplet and quadruplet structures such as shown in FIG. 6C can also be used for each element). The progressive reduction of the mobility ion beam size from a 8 mm² open area multi-hole aperture (corresponding to the usual 1/8 inch *diameter-opening*) to a 0.07 mm² multi hole-aperture (corresponding to the usual 300 μm diameter-opening) is schematically illustrated. The diameter of the circular array will be reduced from 5.37 mm to 0.508 μm. The focusing effect shown in FIG. 6 and the gradual reduction of the open area will minimize the ion loss as the cooled ions are transported from the mobility cell to the high vacuum region of the o-TOF MS. Another way to improve the transmission into the mass spectrometer is to use the focusing effect of the multi-hole electrodes by gradually changing the distribution of the holes to change the beam profile from its initial circular spot to a narrow horizontal rectangle (FIG. 7; not to scale). A gradual change of the ion beam profile from circular to horizontal slit-like shape produces a more focused and parallel beam in the orthogonal TOF MS extraction region. Being able to change the mobility ion beam shape before the ions exit into high vacuum (in which case complicated octopole focusing elements would need to be used) gives many practical advantages. In addition to reducing space charge losses of the mobility ion beam as it is tightly focused to pass through a single exit aperture and in addition to improving the differential pumping performance, this particular beam shape change optimizes and improves the o-TOF transmission and mass resolution. The arrangement of the aperture holes will gradually evolve from circular to rectangular and narrow. The creation of a focused and parallel beam entering the extraction, region enhances the mass resolution in the o-TOF MS.

The electrode pairs may, for example, be made from adhesiveless copper-polyimide-copper laminates with laser-drilled holes or even mechanically punched hole arrays.

Dielectric Coatings for Ion Focusing

The transmission of ions through an orifice such as a skimmer orifice or the entrance of the mobility cell can be further improved by coating the area around it with a special thin insulating film. If a certain amount of positive electrical charge (for positive ions, for negative ions the charge would be negative) is induced on the surface of the film, the mirror negative charge layer is immediately created in the conductor at a distance from the surface equal to the thickness of the film (the surface of the conductor is a mirror surface) forming surface dipoles with short range electrical field. The ions approaching the orifice away form the axis are not lost in a collision with surface but are reflected back by this field. Since the range is short, they are then attracted and reflected again. If there is a transversal component of the electrical field near the wall, the "bouncing" ions begin to drift towards the orifice till they reach it and go through. Thus a collection from an area much wider than that of the orifice itself is achieved.

There is an optimum thickness of the insulating film that is able to retain necessary amount of charge to produce a field strong enough for ions with typical energy distribution to be reflected. The density of the surface charge on the film is restricted by the field strength inside the film which should be less than the breakdown limit. For usual dielectrics this limit is about a few million Volts per cm. The field inside the film is proportional to the charge density on the surface, inversely proportional to the permittivity of the material of the film and does not depend on the thickness of the film. For example, charge density of $10^{12}$ elementary charges per 1 $cm^2$ provides the field strength inside the film of about $10^6$ V/cm for a film which has a typical permittivity of 2. For the 0.1 $\mu$m thick film there is a 10 V potential difference between the surface and the conductor. In most cases this is sufficient for ions moving along the surface to be reflected as ion temperature for complex ions can be only a few times larger than the room temperature, or the "orthogonal" (to the surface) part of their kinetic energy cannot be much larger than 0.1 eV. Otherwise ions would decompose very fast. For such film thickness, the electric field becomes negligible from 1 $\mu$m away from the surface. It means that such films are suitable for coating the walls of channels and tubes of 10 $\mu$m diameter and larger. However when large mass ions move orthogonally or close to orthogonal direction to the surface they may have more energy. In this case the thickness of the film should be increased proportionally to the energy of ions of their motion in the direction orthogonal to the surface. The charge can be induced by several methods. First, it can be a spontaneously induced by the ions of analyte/matrix impinging onto the surface. Once critical density is achieved, the ions are reflected and this density level is maintained automatically. In order to accelerate this process (particularly in case of low ion fluxes) a preliminary charging by a low intensity electrical discharge in gas can be performed. Care should be taken in order not to damage the coating by the discharge.

Figure 9:
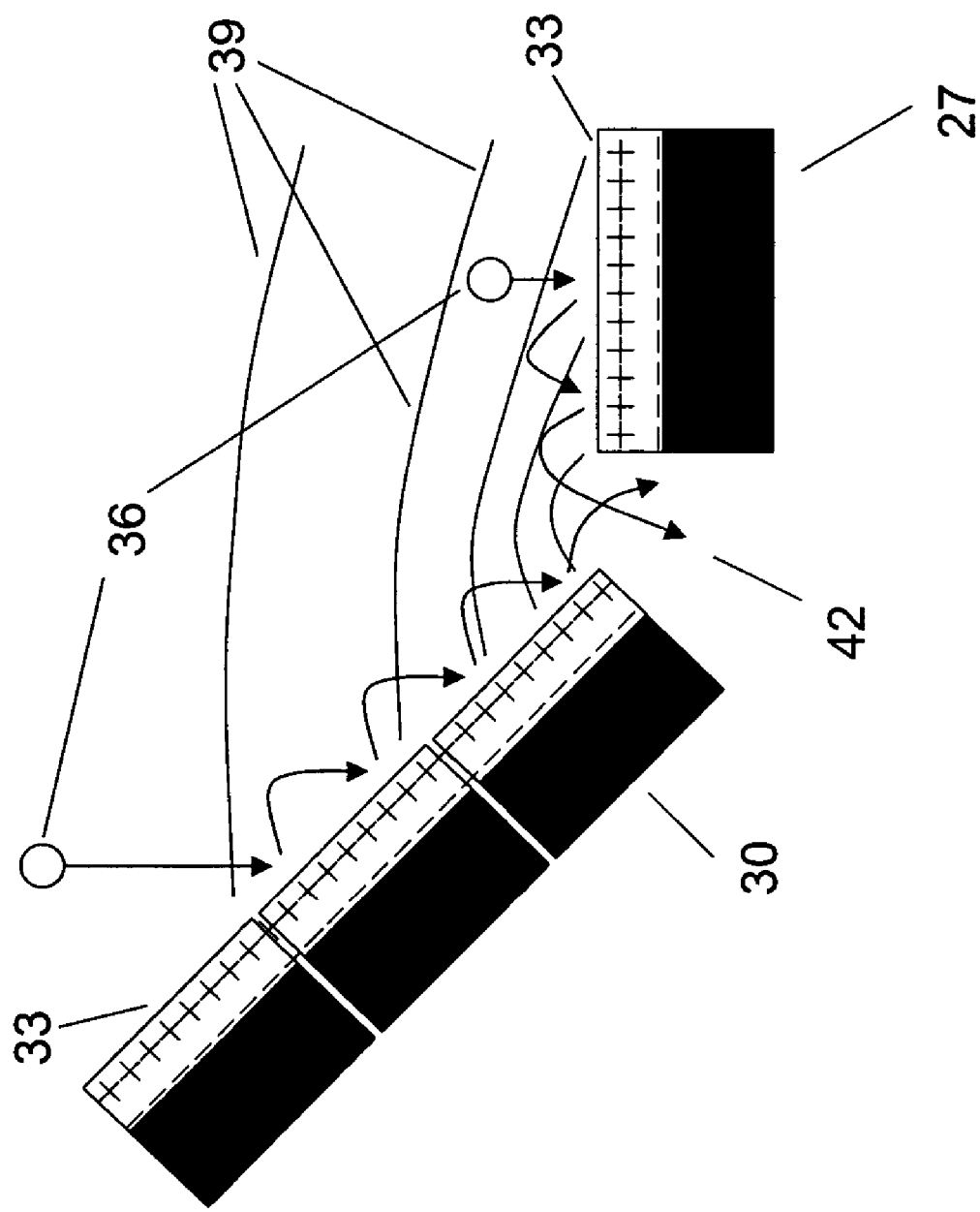
FIG. 9. Induction of a surface dipole on a highly polarizable material using a conical (left) or flat film-coated orifice.

It is possible to induce a surface dipole in a highly polarizable material such as, for example, a piezoelectric thin film e.g. PZT (lead zirconate titanate or $Pb(Zr_xTi_{(1-x)})O_3$) film by having additional biasing electrodes implanted on the surface. FIG. 9 shows two possible approaches that involve either a flat (27) or conical (30) surface, coated with a piezoelectric thin film (33) around an orifice (42). Negative charges which initially were formed on the film surface close to the conductor should be totally compensated by corresponding positive charges on the conductor surface so they are not shown. A segmented conical surface (with increasing negative voltage towards the orifice) is a preferred configuration since it provides a strong component of the field (39) along the surface that helps to push in the direction of the orifice the ions that are randomly reflected. Incoming ions (36), by their reflections on the wall, are focused towards the orifice due to the field curvature are shown. It should be obvious that this type of structures could be applied to any of the electrode areas within the mobility cell to reduce ion loss and improve focusing within the cell as already mentioned, for example, in FIG. 6C. This structure can also be coated with a dielectric thin film and RF voltages can also be individually applied to the segmented electrodes.

The use of piezoelectric structures at strategic places (e.g., collision induced dissociation gaps 9 and 11 in FIG. 1) within the mobility cell is also a convenient way to create a gas discharge which can be used to promote a desired chemical reaction or achieve molecular ion fragmentation.

CID in the Mobility Cell

Figure 10A:
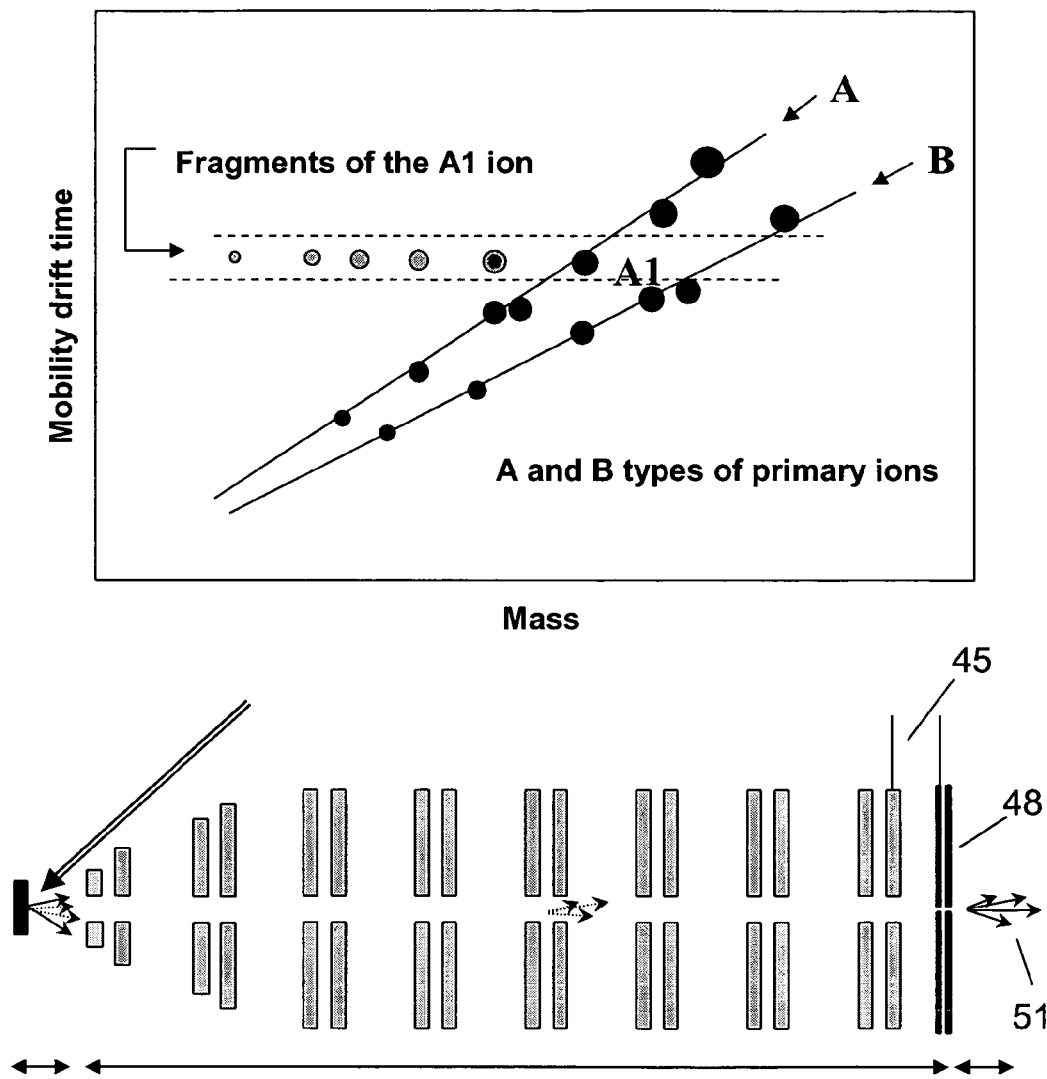
FIG. 10. Two-dimensional representation of the mass-mobility spectrum of a complex mixture of molecular ions (top) and corresponding instrumental platform (below): 10A, the fragmentation occurs at the end of the mobility cell; 10B, the fragmentation is performed in the middle of the mobility cell.
Figure 10B:
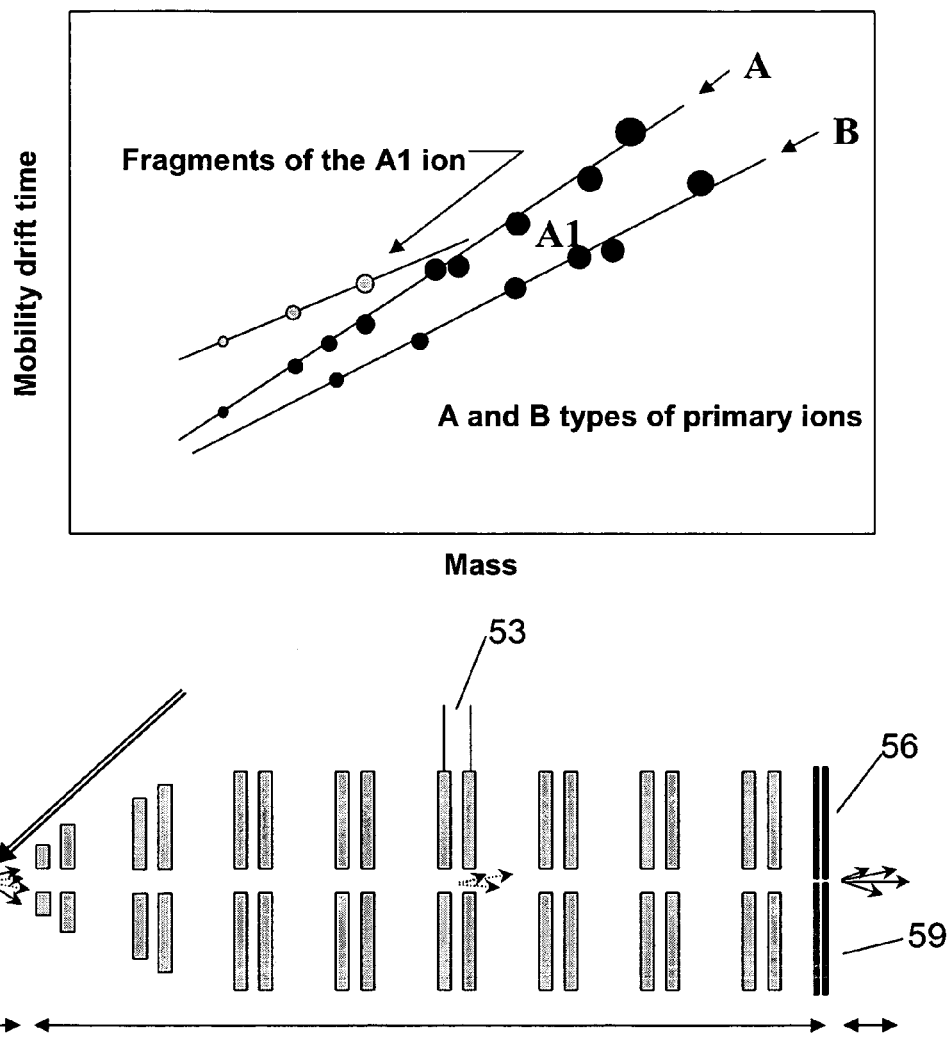

Another possibility using this type of mobility cell is also illustrated in FIGS. 10A and 10B, which demonstrate a two-dimensional representation of the mass-mobility spectrum of a complex mixture of molecular ions. Ions of different classes (e.g., peptides and lipids) form different "trend lines". If only ions of a specific mobility drift time range (marked with dashed lines) fragment, all the fragments are aligned along a separate trend line. In FIG. 10A, the fragmentation occurs at the end of the mobility cell; in FIG. 10B the fragmentation is performed in the middle of the mobility cell. It is of further advantageous to use two or more collision induced dissociation (CID) regions along the cell. In FIG. 10A, the CID gap (45) is at the end of the drift cell near the exit electrode pair (48). Cooled ions (51) exit the cell. In FIG. 10B, the CID gap (53) is in the middle of the mobility cell. This configurations also has an exit electrode pair (56), with cooled ions (59) exiting the cell. All other components are as described for FIG. 1. The voltage between selected adjacent electrodes can be increased to a level where high kinetic energy collisions start to fragment the analyte ions. Here again, very high voltages can be applied without inducing electrical discharge in the carrier gas because of the mean free path length of the carrier gas is longer than the distance between electrodes and this represents considerable improvement over other such dissociation devices which have been previously propose in the prior art. The dissociating voltages can be applied either in DC mode so that all ions going through the region undergo fragmentation, or by applying a short voltage pulse, or laser pulse, or glow discharge pulse so that only ions present in the gap at the time of pulse application are decomposed. If the ions have been previously pre-separated in time by their shapes, only ions with a certain collision cross section will be fragmented. When they are detected by the mass analyzer, they fall onto different "trend lines" in the two-dimensional mass-mobility spectrum (FIG. 10A), thereby improving overall resolution. These lines are usually formed by molecules of similar shape and structure but different mass (such as peptides, or lipids).

As shown in FIG. 10A, the trend line of the fragments of the parent molecule A is parallel to the x-axis contrary to the parent trend lines. The knowledge of the source of fragments thus can allow obtaining structural information (sequence) of the parent ions without any additional MS stage.

If the fragments (as well as parent ions) are allowed to further travel through the remainder of the cell (for example, if the CID (53) is performed in the middle of the cell), they are further resolved. As a result, fragments now align along their own separate trend line (FIG. 10B). If an additional (either DC or pulsed) CID stage is implemented at the end of the mobility cell, it is possible to perform further selective fragmentation of these fragments. These selective fragmentations, in effect, produce an instantaneous multiple MS setup. The feasibility of further $MS^n$ stages is only limited by the necessity of additional stages which may ultimately limit either mobility resolution or ion transmission into the mass spectrometer.

The fact that the fragmentation occurs inside the gas filled cell guaranties the collisional cooling of the fragments. This maintains high mobility and mass resolution for both parent and daughter ions, because it allows forming high quality ion beams at the exit of the mobility cell.

The vacuum enclosure of the mobility cell can be easily achieved by placing viton O-rings between electrodes and compressing the whole structure. Since the vacuum requirement for this section is not very strict (the pressure is in the Torr range), little compression is enough to maintain the purity of the mobility carrier gas. Alternatively, optically transparent glass can be used to allow introduction of photon beams for promoting ionization or ion (or electron) molecule reactions.

Mobility Cell in an Atmospheric Interface

Figure 11:
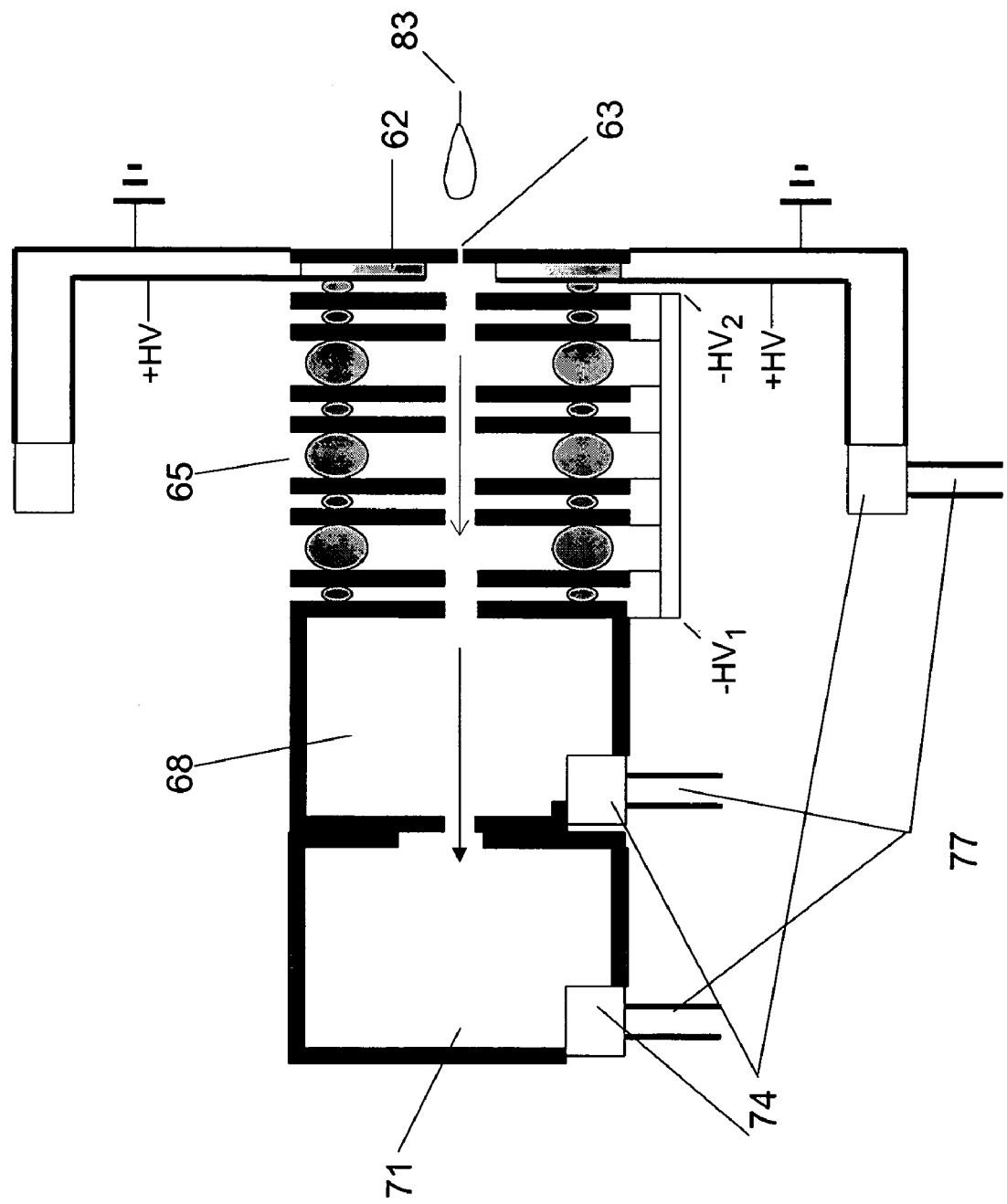
FIG. 11. Schematic of a mobility cell in an atmospheric interface mass spectrometer.

The small gapped electrode structure can be used to improve ion transmission from a high pressure or atmospheric pressure region into a lower pressure mobility cell as shown in FIG. 11, which is a cross-sectional schematic of an atmospheric ion mobility mass spectrometer. The key is a porous semiconductor (62) which can be used to split the gas flow after the ion pass the entrance aperture (63) separating the ion source (83) from the mobility cell. The semiconductor can be biased positively to repel the positive analyte ions and keep them from following the gas flow into the pumps. The first electrode of the mobility cell is at high negative voltage so that the field penetration up to the entrance aperture also helps to preferentially drag the positive ions down the axis of the mobility cell. After exiting the drift cell (65), the ions enter a differential pumping interface (68) and mass spectrometer (71). Electrically isolated vacuum breaks (74) with pumping (77) are used throughout the instrumental platform.

Several of these porous semiconductor pumping structures (62) can be interspersed along the length of the mobility cell. The function of any of these structures can either be to take gas out of the cell or it can be used to put a specific type of gas into a localized region of the cell for purposes of chemical ionization. For example, a narrow gas region can be preferentially biased to such a high field so that fragmentation takes place. If one of the "pumping" structures exists in this small gap region, then it can be used to inject a gas stream which can chemically ionize some of the fragment ions.

Another possibility is to coat the surface of the porous structure with a piezoelectric ionizer structure which could be used to initiate a glow discharge at will within the ion mobility cell in a specific region. A reactive gas can be injected through the porous semiconductor at the same time into this discharge region so that the ions that are in this mobility region can be fragmented or chemically adducted.

Potential applications for this type of a drift cell comprise, but are not limited to 1) Ion mobility drift tube in the combination Ion Mobility and High Pressure MALDI Mass spectrometry; 2) Ion mobility drift tube in the combination of Ion mobility and Secondary Ion Mass spectrometry; 3) Pressure interface for the high pressure sources, such as Electrospray Ionization and Atmospheric Pressure MALDI. The difference between the systems is the pressure in the region where the ions are formed. For Medium Pressure MALDI, ions are generated at similar pressures to that of the mobility cell (a few Torr). For SIMS, ions are formed in higher vacuum (a few mTorr) and travel against the flow of the carrier gas as they enter the drift cell. When the drift cell is used as an interface, the pressure in the source region is higher (up to 1 atm). In the latter case an additional differential pumping of the cell is required. If the influence of the gas fluxes or the ion diffusion can be minimized or used for the benefit of the high transmission, the same basic design can be applied to all this variety of applications.

Computer Simulation Results

The following computer simulations were performed for the Ion Mobility interfaces with Medium Pressure MALDI MS and SIMS. Different geometries and sizes of electrodes were tried in order to optimize the transmission and resolution of the drift cell. The total length of the mobility cell was lower then what is used in the experimental design due to the limited computational power, but the simulation tries to closely imitate the geometry and the field distribution.

1. MALDI

A. 3-cm Long tube/20 Ring Electrodes

Simulations performed for the following set of parameters in a 3 cm long cell show a transmission of about 30% when applying a total axial field of 1200 V for two types of singly charged ions with the initial energy of 1 eV and masses of 360 and 720 a.m.u. with the same or similar collision cross sections. Under these conditions, there is no decomposition of ions inside the drift cell.

Figure 12:
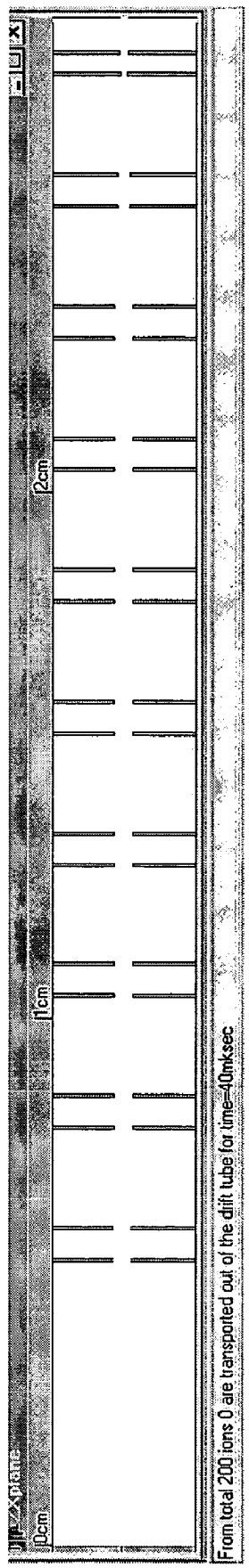
FIG. 12. Simulation showing two types of ions (black and gray) moving in a 20-electrode, 3 cm-long cell under 1200 V and a 2 Torr He pressure.
Figure 13:
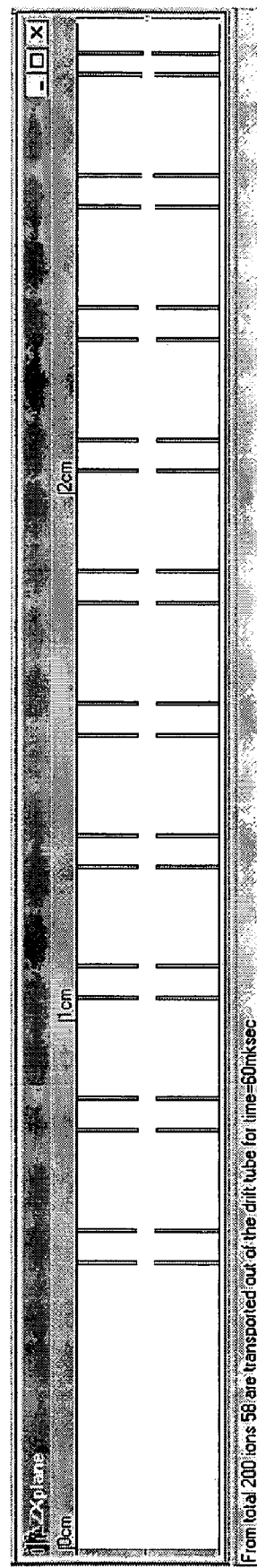
FIG. 13. Same simulation as described in FIG. 12 at time of ion arrival at end of drift tube; ion transmission is about 29%. This screen copy is taken when the ions have arrived.

Helium gas pressure: 2 Torr
Electrode thickness: 0.1 mm
Distance between paired electrodes (which is close to the free path length of electrons in 2 Torr He): 0.5 mm
Distance between pairs: 2 mm
Initial inner ring diameter: 1.6 mm
Inner diameter of the ring pair before the exit pair: 1 mm
Inner diameter of the exit pair: 0.3 mm
Distance between the two last rings: 0.3 mm
Initial beam size: 0.3 mm The results of simulations in these conditions are shown in FIG. 12 and FIG. 13. FIG. 12 is a snapshot taken when ions travel inside the tube. The mass of the darker ions is 360 amu and they have a 116 $Å^2$ cross-section. The mass of the lighter ions is 720 amu and they have a 116 $Å^2$ cross-section. The field in the ionization interface is 200 V/cm. The initial ion beam energy and diameter are 1 eV and 300 µm, respectively. The electrode thickness is 100 μm. The distance between paired electrodes is 500 μm and between pairs 2 mm. The inner ring diameter is 1.6 mm except for the pair before the exit pair (1 mm) and for the exit pair (300 μm). This snapshot of the simulation is taken when the ions have already traveled through roughly ⅔ of the drift cell (after 40 μs). No ions are lost by decomposition or discharge on the ring surface. The estimated resolution is then about 20. FIG. 13 illustrates the end of ion travel inside the drift cell. Fifty-eight ions out of initial 200 are transmitted through the orifice. The overall transmission is about 30% and the resolution is at least 20. Ions are lost at the before-last electrode pair and the exit electrode pair. The simulation software, also provides the standard deviation and arrival time. The resolution can then be calculated knowing that for Gaussian peaks, the full width at half maximum is a standard deviation multiplied by 2.35.

Figure 14:
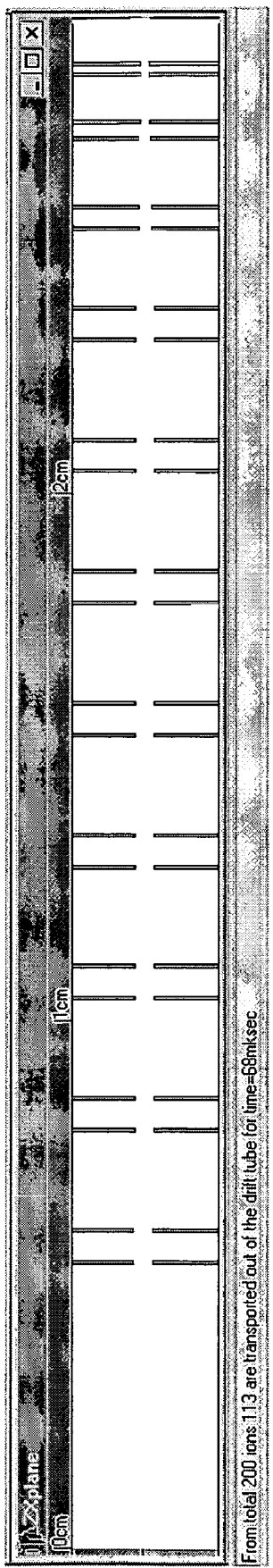
FIG. 14. Same simulation as described in FIG. 12 with potential modified between electrodes in last three pairs; ion transmission is about 56%.

When the potential between electrodes in the last three pairs is doubled, ion transmission greater than 50% is achieved (FIG. 14). Applying a larger axial voltage of 1800V instead of 1200 V increases the ion transmission to the value of about 60%. FIG. 14 shows the same ion motion conditions as described in FIG. 12 with modified (field in the ionization interface set at 100 V/cm). The cell is slightly different from the cell described in FIG. 12. The gap between paired electrodes of the three last pairs is gradually reduced as well as their inner diameter. The potential difference in the last three pairs is twice the potential difference in the other pairs. This snapshot is taken when the ions have arrived. The overall transmission is about 55%. Ions are lost at the three last electrode pairs.

B. 3-cm Long Tube/12 Ring Electrodes

Figure 15:
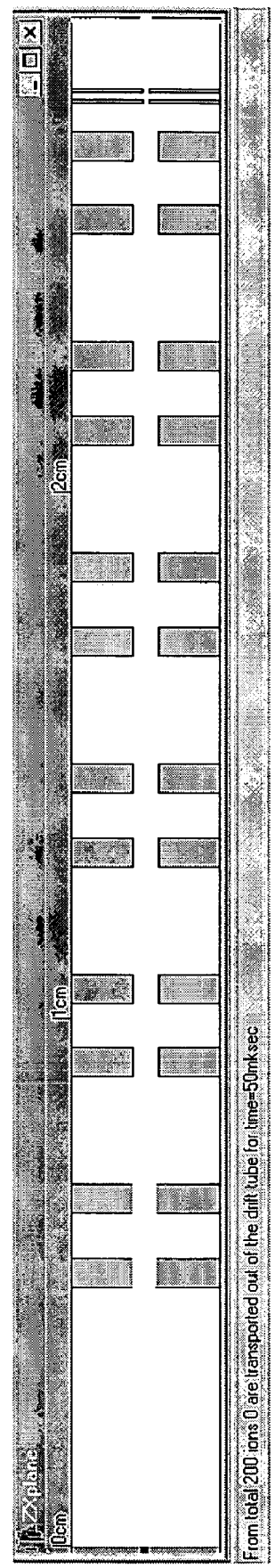
FIG. 15. Simulation showing two types of ions (black and gray) moving in a 12-electrode, 3 cm-long cell under 1200 V and a 2 torr He pressure.
Figure 16:
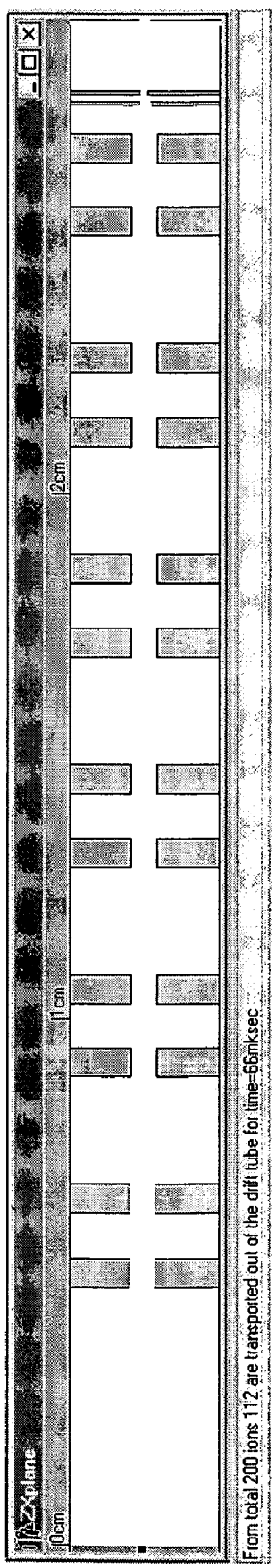
FIG. 16. Same simulation as described in FIG. 15 at time of ion arrival at end of drift tube; ion transmission is about 56%.

In a cell of the same length but with fewer and thicker electrodes, 112 out of 200 initial MALDI ions pass through; this is more than 50% of ion transmission at the same He pressure and total voltage (see FIG. 15 and FIG. 16). In FIG. 15, the mass of the red ions is 360 amu and they have a 110 $\text{Å}^2$ cross-section. The mass of the lighter ions is 720 amu and they have a 116 $\text{Å}^2$ cross-section. The field in the ionization interface is 100 V/cm. The initial ion beam energy and diameter are 1 eV and 1 mm, respectively. The detailed parameters are:

Electrode thickness: 0.6 mm except for the exit pair
Distance between paired electrodes: 0.8 mm
Distance between pairs: 4 mm.
Initial opening diameter: 2.2 mm.
Opening diameter of the ring pair before the exit pair: 1 mm
Opening diameter of the exit pair: 0.3 mm
Distance between the two last electrodes: 0.1 mm.
Initial beam size: 1 mm This snapshot (FIG. 15) of the simulation is taken before the ions reach the exit electrode pair. Few ions are discharged on the first ring electrode. The estimated resolution is 13 for the light ions and 18 for the heavy ions. In FIG. 16, the conditions are the same as those of FIG. 15, and the snapshot is taken when the ions have arrived. The overall transmission is about 55%. Few ions are lost at the first ring but most at the exit electrode pair. In comparison with the previous design, the distance between two last pairs is limited to 0.5 mm to reduce the ion diffusion and beam divergence. For the same reason, the distance between exit electrodes is 100 μm. The resolving power is similar to the previous case. Four ions out of initial 200 are lost discharged on the entrance electrode.

Figure 17:
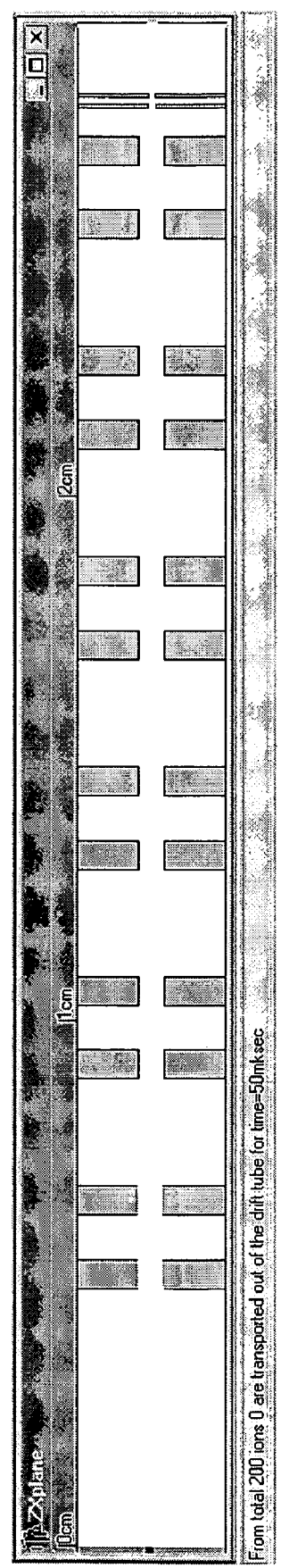
FIG. 17. Same cell characteristics and simulation parameters as described in FIG. 16 except that a higher overall axial voltage is applied (1800 V instead of 1200 V).
Figure 18:
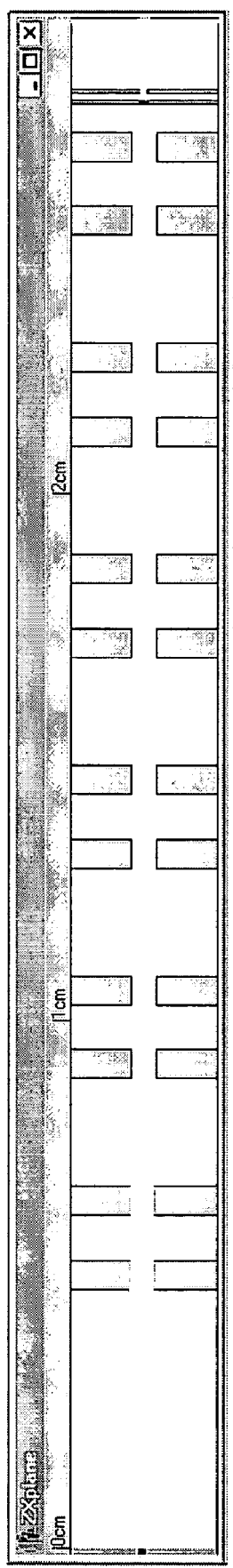
FIG. 18. Same simulation as described in FIG. 17 at time of ion arrival at end of drift tube; ion transmission is about 71%.

For a higher axial voltage (1800 V) along the cell (see FIG. 17 and FIG. 18), the ion transmission is about 70%. Applying an RF-voltage between electrodes does not improve the results. FIG. 17 has the same cell characteristics and simulation parameters as described in FIG. 16 except that a higher overall axial voltage is applied (1800 V instead of 1200 V). This higher field leads to a lower ion loss at the entrance electrode. This snapshot is taken just before ions go through the last electrode pair and shows a highly focused beam. The estimated resolution is then 17 for the light ions and 12 for the heavy ions. FIG. 18 also is the same simulation as described in FIG. 17, at time of ion arrival at end of drift tube. The overall transmission is 71%. Ions are mainly lost at the exit electrode pair.

Figure 19:
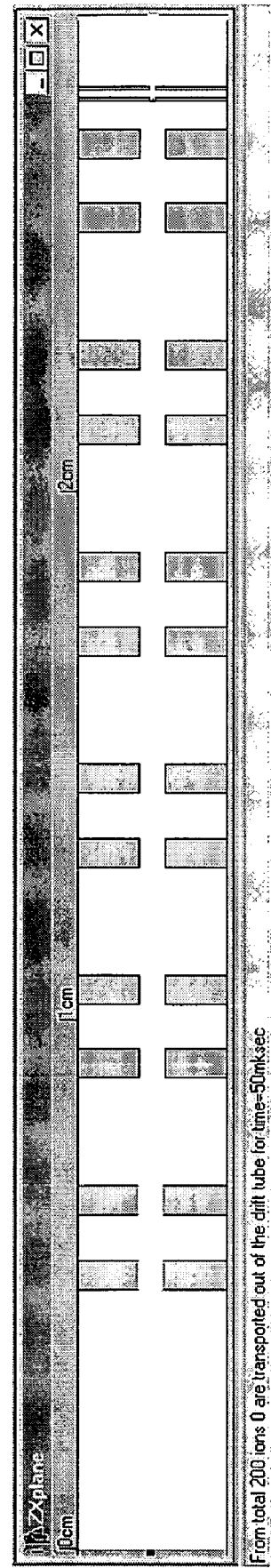
FIG. 19. Same cell characteristics and simulation parameters as described in FIG. 15 except that a 100 V-RF voltage is superimposed to the DC axial voltage (1200 V).
Figure 20:
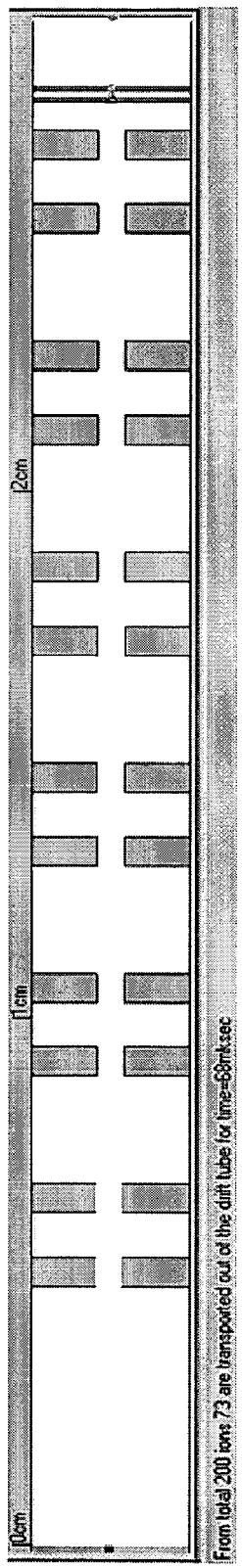
FIG. 20. Same simulation as described in FIG. 19 at time of ion arrival at end of drift tube; ion transmission is about 36%.

FIG. 19 and FIG. 20 show results for a 100 V RF-voltage. A noticeable number of small ions are decomposed at the end of the cell. Hence only 73 out of the initial 200 ions exit the cell. The simulation of FIG. 19 uses the same cell characteristics and simulation parameters as described in FIG. 15 except that a 100 V-RF voltage is superimposed to the DC axial voltage (1200 V). The snapshot of FIG. 19 is taken just before ions pass the last electrode pair. In contrast with what simulations for periodic field cells demonstrate, the addition of an RF field does not improve the focus. The estimated resolution is 14 for the light ions and 12 for the heavy ions. FIG. 20 shows the same simulation as that in FIG. 19; the snapshot being taken when the ions have arrived at the end of the drift cell. The overall transmission is lower than without RF (36% versus 55%).

2. SIMS

Figure 21:
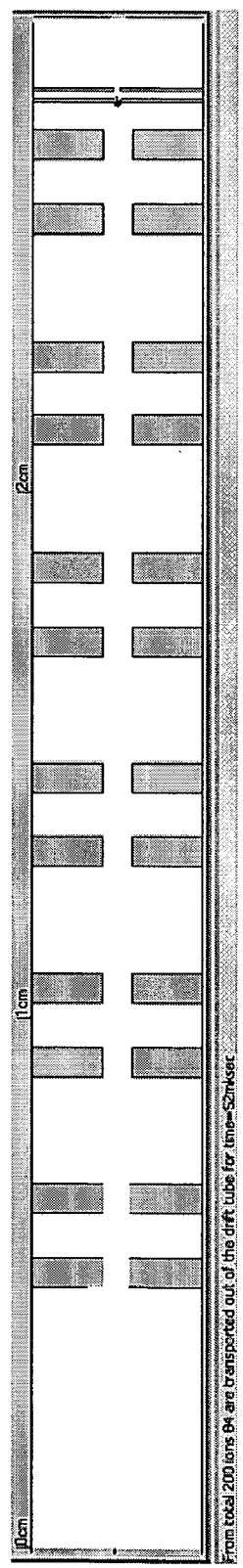
FIG. 21 Same cell electrode characteristics and configuration as described in FIG. 15 monitoring the transmission of SIMS ions; ion transmission is about 42%.
Figure 22:
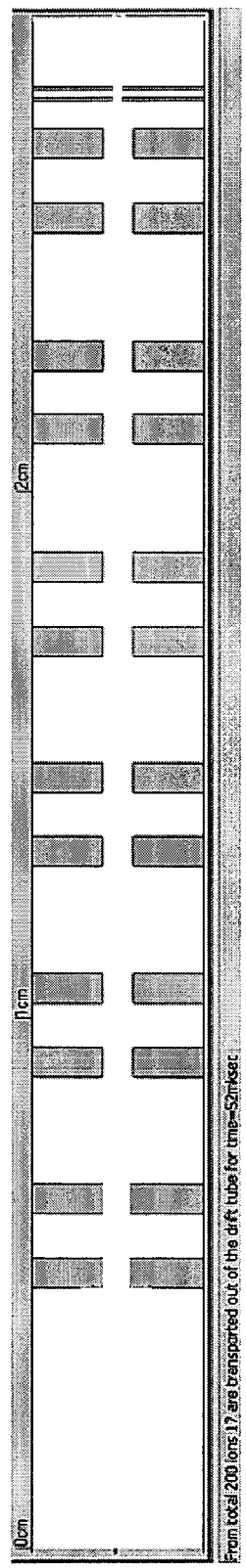
FIG. 22. Same cell characteristics and simulation parameters as described in FIG. 21 except for the higher beam energy (1 eV instead of 0.1 eV) and field in the ionization interface (50 V/cm); Ion transmission is about 9%

For the same cell as used in section 1.B. above (and a pressure of 10 mTorr in the ion formation region, the transmission of the SIMS ions is lower than that with a MALDI source; about 40% and 10% for ions having initial energy 0.1 eV (FIG. 21) and 1 eV (FIG. 22), respectively. Most ions are lost on the entrance electrode. Ions making through the entrance orifice are focused and transmitted through the first electrode of the exit pair. Coating the entrance aperture with thin insulator or using piezoelectric thin films, which themselves may be coated with a thin insulator, can markedly improve this transmission against the mobility gas counter-flow.

3. Testing of the Cell Prototype by Using Atmospheric Corona Discharge and Direct Current Measurements.

Figure 23A:
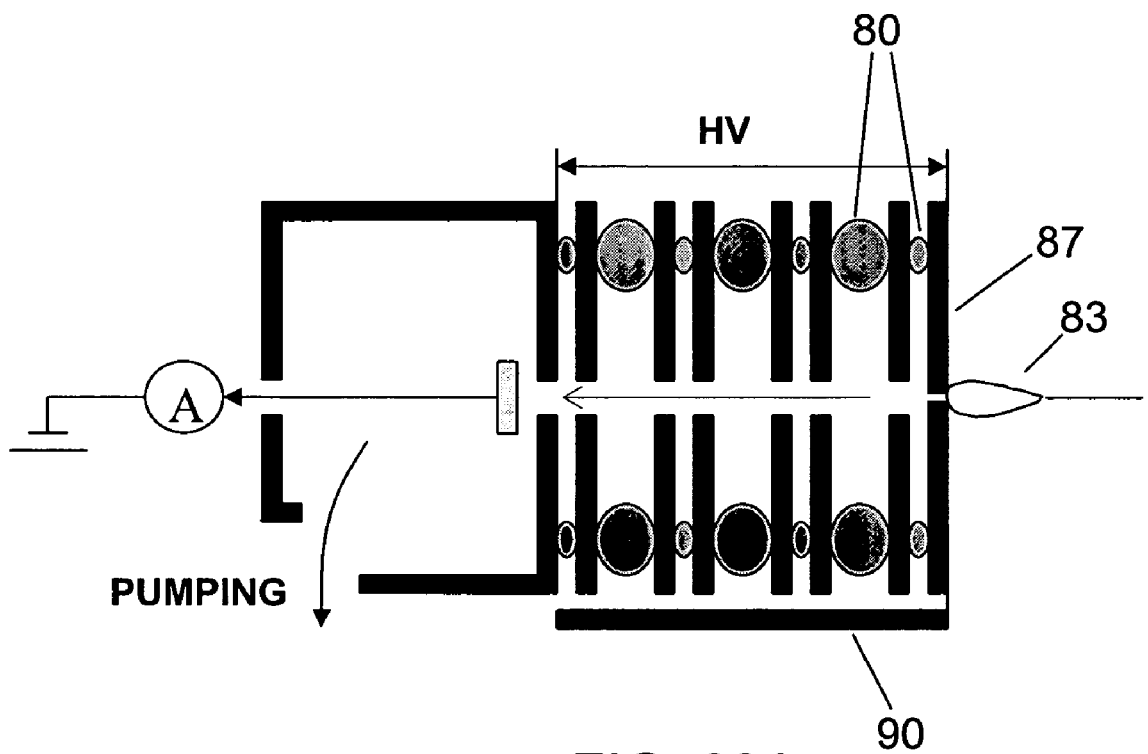
FIG. 23. Schematic of mobility cell breakdown voltage and transmission testing setup; 23A, wide opening at the skimmer; 23B, narrow orifice and side openings.
Figure 23B:
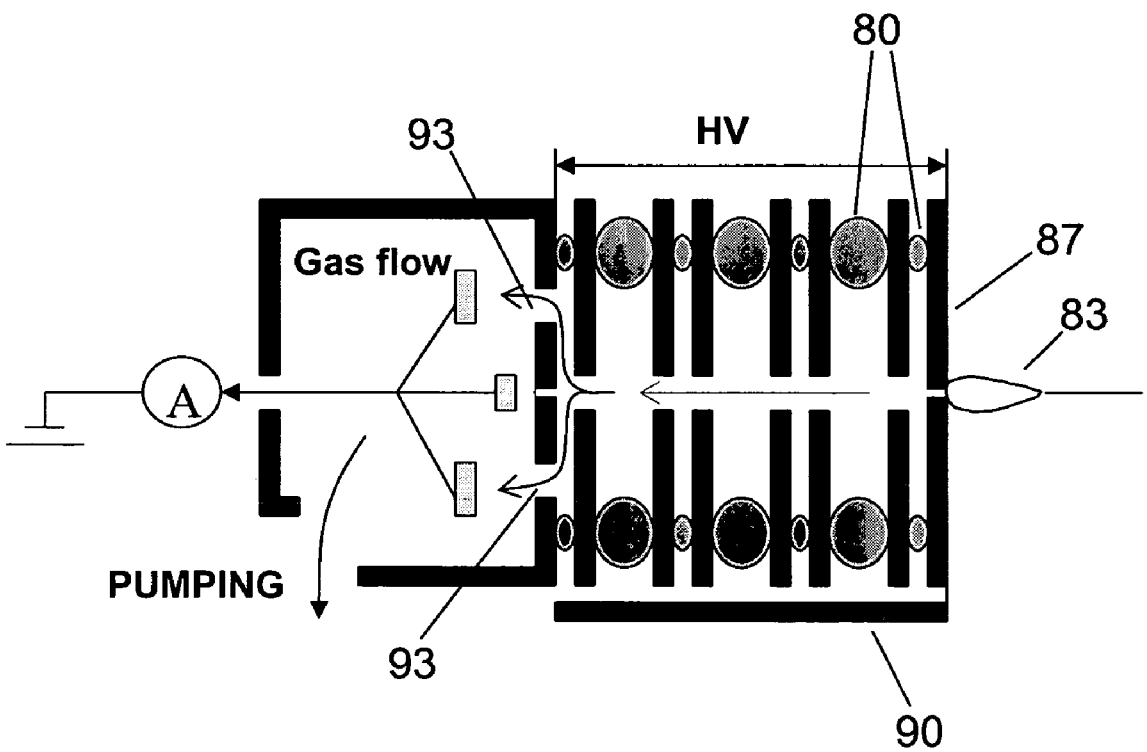

The instrumental platform is shown in FIG. 23. Two modifications of the cell were tested. In the first one (FIG. 23A) a short (0.7″) cell was pumped from the back side through the wide (2.2 mm diameter) opening. The air pressure was maintained around 2 Torr. The vacuum insulation was provided by the use of O-rings (80) of different thickness, which also served as variable spacers. The corona discharge created by applying high voltage between the sharp wire tip (83) and the entrance electrode (87) served as an ion source. The electrodes were connected by a resistor chain (90) to provide necessary voltage drops. This setup allows estimation of the maximum voltages that can be applied between the electrodes and across the entire cell, and estimation of the ion losses on the electrodes.

The dimensions and spacing of the 4 pairs of electrodes were similar to those of the simulation 1*b*), but did not include a small aperture. It was possible to apply up to 600 V between individual electrodes separated by only 0.6 mm, and the maximum total voltage was only limited by the power supply capability. The transmission was measured at bias voltages of up to 1700 V across the entire cell.

To estimate the divergence of the ion beam the current on the electrode placed immediately after the last cell ring was compared to the current entering the cell (all electrodes shorted). The current measurements demonstrate that practically no ions are lost on the intermediate electrodes at 1700 V across the mobility cell, whereas when no voltage is applied the transmission is only about 20%, and it is probably determined by the efficiency of the ion transport in the gas flow from the region of high pressure towards the pumping port.

Using a two times longer (1.5") cell in the same setup, a transmission of more than 50% was detected. A more direct transmission measurement was produced in the second modification of the instrumental platform (FIG. 23B), where an actual orifice (500 μm diameter) was introduced at the end of the cell. To maintain the similar pressure regime, two additional peripheral openings (93) in the skimmer were made. All other components are as indicated for FIG. 23A. The measurements revealed that due to the presence of these side holes, the gas flow at the skimmer aperture is perpendicular to the axis of the cell, and the ions are entrained towards the periphery. Thus, the transmission through the aperture went from 0.1% with no voltage applied to 6–7% at 1700V—significantly less than in the case of no aperture. At the same time, the ion current through the side openings does not change with the voltage. These results suggest that in order to achieve high transmission through the skimmer aperture, a divergent gas flow in the vicinity of the orifice must be avoided.

This condition is automatically fulfilled for the MALDI-IM experiment where the pressures in the sample region and in the cell are the same. When using the cell as a high pressure interface, additional measures have to be taken in order to prevent the ion diffusion due to the flow of gas that is being differentially pumped.

The results of these preliminary tests show that the proposed configuration of electrodes allows one to apply significantly higher voltages compared to a periodic field cell with equally spaced electrodes, and that the field configuration helps to confine the ions within a narrow region close to the cell separation axis.

4. Testing of the Cell in MALDI-IMS o-TOF Setup

Figure 24:
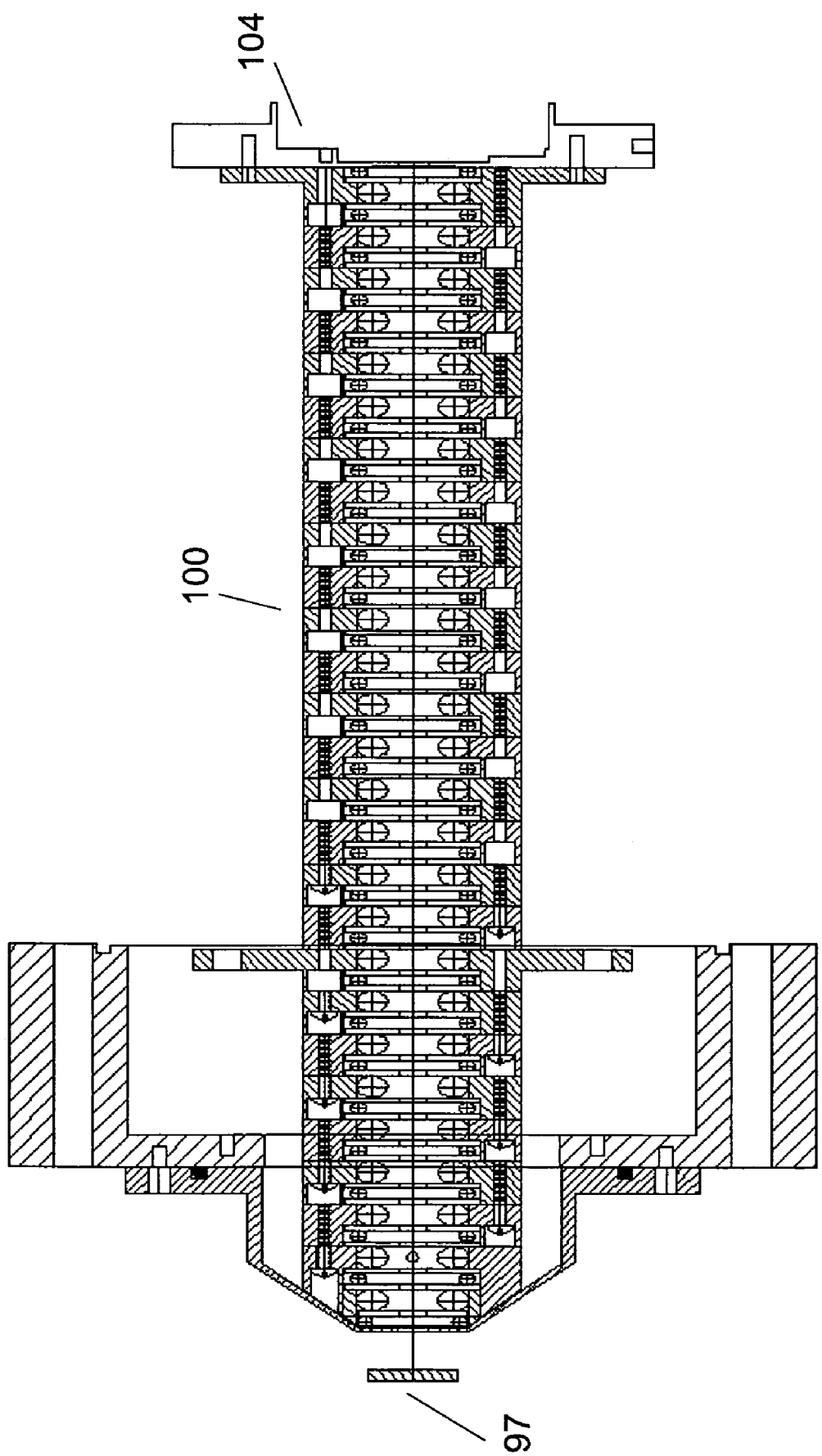
FIG. 24. Copy of an AutoCAD drawing of the cell mechanical design.

Testing of the new mobility cell was performed in combination with compact orthogonal time-of-flight mass spectrometer and a MALDI source. FIG. 24 shows the experimental setup with sample (97), mobility cell (100), and mass spectrometer (104). A test cell with the following parameters was tested.

Electrode thickness: 0.625 mm
Distance between paired electrodes: 1.250 mm
Distance between pairs: 2.500 mm
Opening diameter: 3 mm
Skimmer orifice diameter: 0.500 mm
Number of electrodes: 56
Total cell length: 140 mm
Sample-cell distance: 4 mm The cell was tested at a bias voltage of up to 1800V; the sample was biased up to 100V with respect to the cell entrance. The obtained mobility resolution values (up to 40) were close to the ones predicted by simulations for these voltages and geometry.

Preliminary transmission measurements revealed a significant improvement compared to the periodic cell design operated at the same bias voltage. Sensitivity test for the small (1040 a.m.u.) angiotensin II peptide molecule demonstrated a detection limit of 2.5 femtomole. Experiments involving different ratios of the electrical fields in small and large gaps demonstrates an optimum corresponding to a two times higher field in small gaps.

The effect of the placing of the mobility cell entrance close to the sample (at about 4 mm) and using conical electrode design, when compared to the standard 1" separation was found to result in an approximately twofold increase in total transmission.

The new design allows one to apply voltages that are impossible in a regular periodic or linear mobility cell due to the possibility of a discharge. At a certain level (typically about 2000 V), the mobility resolution improvements become negligible while the collision induced dissociation of ions increases. The increase in the cell gas pressure allows avoidance of ion fragmentation at higher fields. However, the requirements for the high vacuum in the mass analyzer section limit the cell pressure to the range below 10 Torr. This pressure limitation can be removed by using higher pumping speed in the mass spectrometer which would allow the mobility cell to be operated at even higher pressures and voltages.

Figure 25:
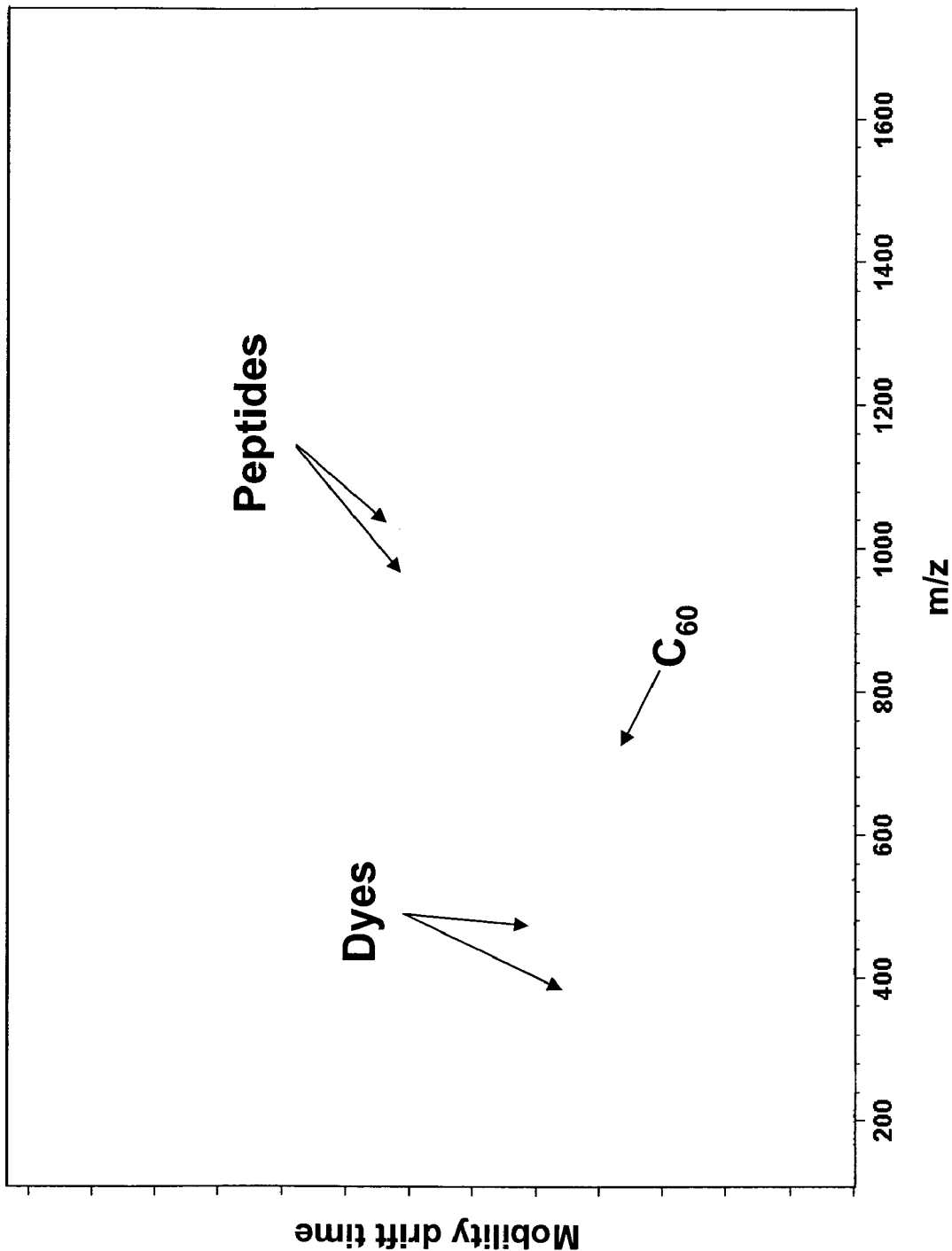
FIG. 25. A typical 2D mass-mobility spectrum obtained using the described mobility cell of FIG. 24.

FIG. 25 shows a typical two-dimensional spectrum obtained using the described instrumental arrangement. Mass/charge is plotted on the X axis, while mobility drift time is plotted on the Y axis. Signals from a mixture containing peptides, dyes and $C_{60}$ are clearly visible. The mobility resolution is in the 30–40 range.

Because of its high transmission, small cross-section/length, high resolution, and the approximately 1–100 Torr operating pressure, there are numerous applications where the new mobility cell is quite useful. One such application is the improvement of laser post ionization secondary neutral mass spectrometers. Such spectrometers rely on processing secondary ions and neutrals which are desorbed from a surface by an energetic particle source or by a photon beam. The m/z ratio of the desorbed secondary ions are determined by a mass spectrometer (usually a time of flight) and then the desorbed neutrals are ionized—usually by a focused laser beam—and their m/z is then determined in the same mass spectrometer. A particularly powerful laser desorption microscope based on this principle is described by Pellin et al. in "TOF-SIMS: Surface Analysis by Mass Spectrometry" (IM Publications, Surrey U.K, 2002), chapter 14, page 375. This spectrometer first desorbs ions by using either a microfocused liquid metal ion beam or a laser beam which is microfocused by a Schwarzschild microscope to a sub micron diameter. The desorbed ions then travel away from the sample. After a suitable period of time (varying from a few hundred nanoseconds to several microseconds depending on the type or molecule or element to be detected), a laser post ionization pulse is applied to a several cubic mm volume which can contain up 30% of the desorbed neutral atoms. The size of this volume must be as small as possible both to minimize the laser power and to improve the mass spectral resolution of the time of flight. On the other hand, the volume must be as large as possible to collect as many of the laser desorbed neutrals as possible. A solution to this dilemma is the addition of an ion mobility cell within the coaxial volume of the Schwarzschild microscope. At present, the design of Pellin uses this coaxial volume for the ion optics which are necessary to transport desorbed ions from the sample into a three meter long traditional coaxial reflector time-of-flight mass spectrometer. Even with the use of such a large spectrometer the achieved mass resolution is only around 1000 from the large spatial volume containing the post ionized neutrals.

In contrast, the addition of the new low profile IM-oTOFMS spectrometer described herein (see FIG. 1) into the small coaxial ion transport volume of the Schwarzschild optics solves these problems. One Torr of helium transport gas first injected onto the sample surface (2) serves to cool both the desorbed neutrals and ions. This cooling restricts the volume into which they expand. The extraction field separates the ions from the neutrals and the ions progress into the IM cell. The post-ionization laser (4) can then be used several microseconds after the initial desorption pulse (1) to intercept the neutral packet which is being slowly drifted toward the mobility cell by the mobility carrier gas flow. Helium carrier gas is transparent to wavelengths into the hard UV so the post-ionization process of the neutrals will not be impeded. The post-ionized neutrals are then transported into the mobility cell where they are resolved according to charge/volume. If there are identical types of directly desorbed ions and post ionized neutral ions from the sample then these identical ions formed from the two processes will appear along parallel trend lines separated by a time equal to the difference of the application of the primary desorption energy pulse (1) and the post-ionizing energy pulse (4). Because the desorption and ionization events are decoupled from the mass analysis and because of the high transmission of the new mobility cell design, utilization of higher than 30% of all desorbed elements and molecules and a mass resolution of 5,000 in a instrument whose physical size is $\frac{1}{20}^{th}$ the size of the existing laser post-ionization spectrometers can be achieved.

Interfacing with the Time-of-flight Mass Spectrometer

Figure 26A:
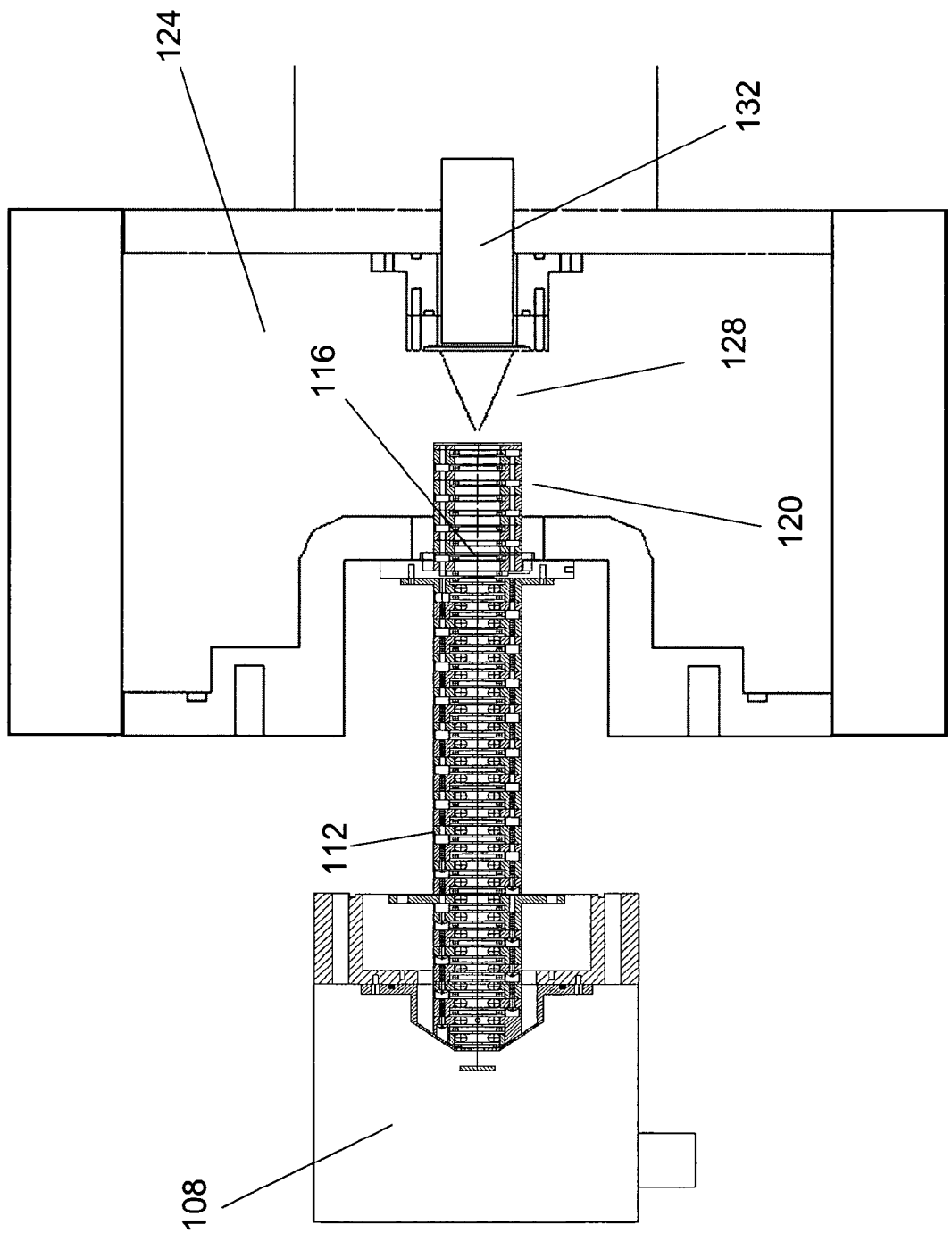
FIG. 26. 26A, combination of a special mobility interface tube with the differential pumping including a conical skimmer; 26B, detailed view of the interface drift tube.

The TOF mass spectrometer requires high vacuum conditions to operate. Therefore, additional measures may be required to make a transition from pressures typical for the mobility cell (1–5 Torr) to the TOF MS section ($10^{-6}$–$10^{-7}$ Torr). These include the use of small orifices and differentially pumped interfaces. FIG. 26A demonstrates the combination of a special mobility interface tube with the differential pumping including a conical skimmer. In this figure, there is a sample introduction (108) at the entrance of the mobility cell (112). Upon exiting the mobility cell (112), ions enter a differential pumping interface (124) through an orifice (116) located between an interface drift tube (120) and the mobility cell (112). Additional focusing to improve throughput is accomplished by the use of the interface drift tube (120). This is followed by a skimmer cone (128) and extractor and beam forming optics (132) which prepare the analyte species for entry into another analytical platform, preferably a time-of-flight mass spectrometer. FIG. 26B is an expanded view of the interface drift tube (120). The mass spectrometer can ideally be one of the configurations using a position sensitive detector as described in the following: U.S. Pat. No. 6,683,299 to Fuhrer et al.; in copending application Ser. No. 10/155,291 to Fuhrer et al. filed on Oct. 20, 2003; and in the U.S. application of Fuhrer et al. filed on Oct. 18, 2003 and having application Ser. No. 10/967,715, which includes the ability to read and keep separate the ion output of multiple IMS channels using only one mass spectrometer.

The use of an extra drift tube placed right after the main mobility cell is based on the necessity to provide a smoother pressure drop after the skimmer orifice, and to form a high quality molecular beam with low divergence and ion energy spread. In a preferred embodiment, these two parameters achieve high resolution and sensitivity of the mass spectrometer. The channel diameter in the interface is larger than that of the mobility cell, and the applied field is lower due to lower pressure. The focusing of ions is achieved using the same method as in the main mobility—by varying the distances between electrodes. If the voltage applied to the gaps between the electrodes is the same, the field is stronger in the small gaps, and there is a field penetration into the large gaps, which produces the focusing effect.

Simulations show that it is possible to achieve the divergence of less than 0.08 rad, and the energy spread of 0.4–0.6 eV. The theoretical transmission of 100% can be achieved with specific voltage settings. At the end of the channel, the pressure is about one order of magnitude lower than in the mobility cell. The next region is evacuated by high speed pumping in order to further reduce the flow of the carrier gas into the TOF. This allows achieving high vacuum conditions in the mass spectrometer as well. Experimental data shows that efficient pumping in this region can achieve the theoretical levels of resolution and transmission of the mobility setup. The pumping also has to be symmetrical in order to avoid preferential side flow of the gas from the orifice which can entrain the ions away from the skimmer. This effect can occur at relatively low pressures and produce further signal losses.

The gas molecules may be skimmed using a conical shape skimmer (or skimmers of different shapes as well). The pressure in the region behind the skimmer is already very low so that ions can be efficiently extracted using only slightly biased TOF primary beam optics.

The effect of using an additional mobility interface section (see FIG. 26) after the main cell has been tested. The experimental data shows that there is no or very little ion loss in the interface. The mobility resolution after the interface is only about 10% lower than the resolution right after the mobility cell. The pressure drop in the interface allowed operating at 2.5× higher pressure and applying 2× higher voltage across the mobility cell. This achieves high resolution using a very short (5") drift cell.

Figure 27:
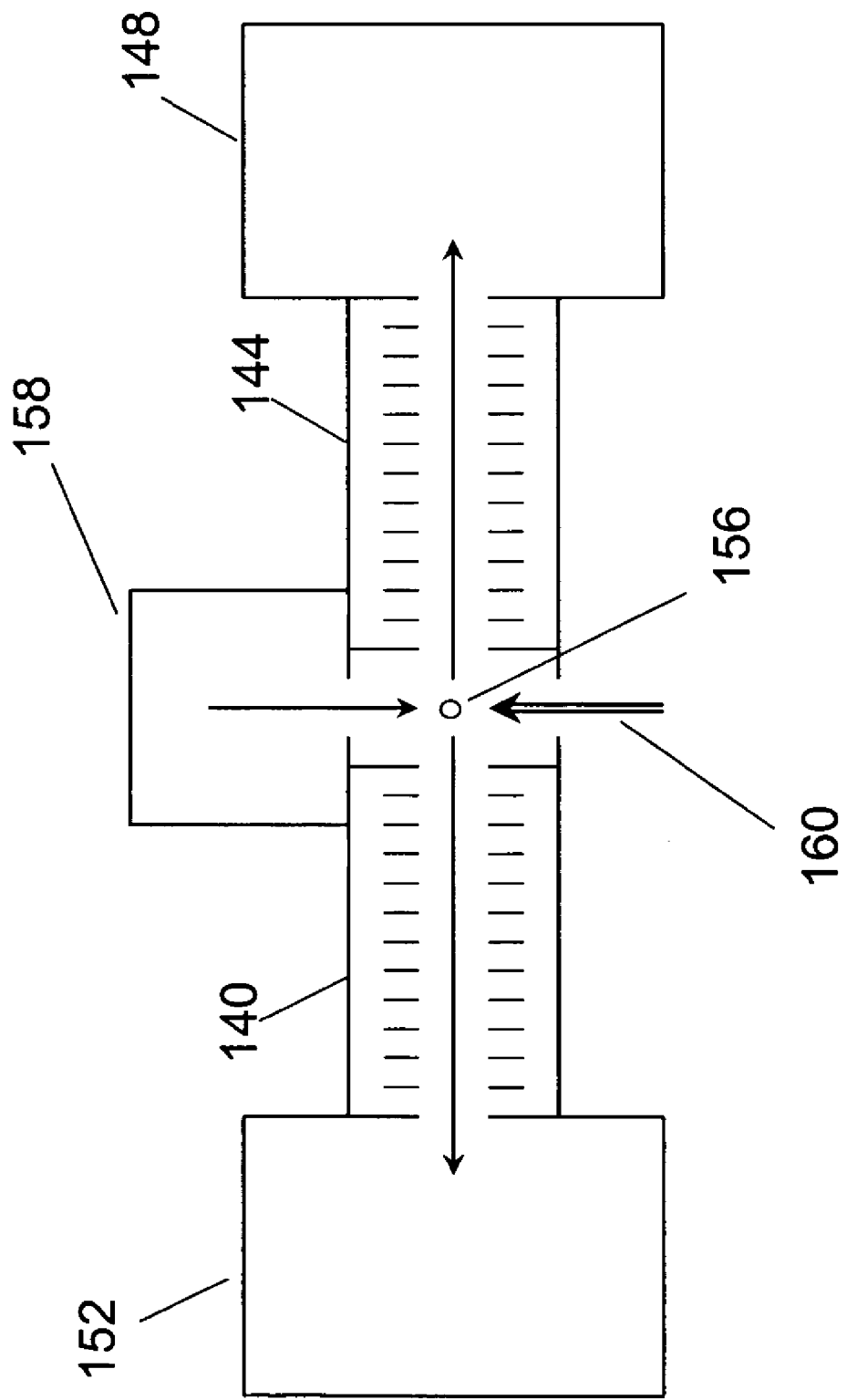
FIG. 27. Schematic of the setup for bipolar mass spectrometry of aerosol particles. Schematic of tandem arrangement for injecting either mobility separated ions, mobility separated ionized particles, or neutral particles into the ionization region between to mobility TOFMS apparatus for separating and measuring mobility and fragmented ions or ions desorbed from the injected particles.

Another configuration suggested by the superior performance properties of the IM-oTOFMS is for laser ablation of aerosol particles or for fragmentation or photoionization of mobility separated ions. It is possible to produce such particles comprising MALDI matrix and analyte or also analyte and small light adsorbing particles which can act as a MALDI substrate for large bio-ions. Such particles can be ionized and transported with a mobility cell or they may alternatively remain neutral and be transported by a flow tub. FIG. 27 schematically illustrates the use of a mobility cell or some other gas transport device (158) to inject ionized or non-ionized particles or molecules (156), i.e., neutral species, into the entrance region between two opposing IM-oTOFMS spectrometers (148 and 152), the region between the two opposing IM-oTOFMS comprising two opposing mobility cells (140) and (144). The two mobility drift cells are configured in a substantially horizontally opposed manner, i.e., having separation axes configured 180° or approximately 180° from one another. In the entrance region, the ion or neutral species may be subjected to a fragmentation source. One of the oTOFMS operates in negative mode, while the other operates in positive mode. After the analyte (156) is injected into this region, it is irradiated with ionizing radiation (160). Both positive and negative ions are created and are transported by the opposing fields into one or the other of the appropriately biased spectrometers. The bias of the entrance to the spectrometers can be controlled by a computer sequence so that the region between the entrance to the mobility cells is field free. Analyte (156) can then drift (either as ions or as neutrals) along with the gas flow which is orthogonal to the axis of the mobility cells. At an appropriate time extraction pulses are simultaneously or sequentially applied to the face of the mobility cells so that ions are extracted into the respective mobility cells according to the ion polarity. At some time later, ionizing radiation can be applied to convert the gas transported neutrals into ions and these post ionized neutrals would also enter the two mobility cells. All of the post-ionization features described previously as referenced to FIG. 1 would apply for both the negative and positive mobility spectrometers. Although FIG. 1 and FIG. 27 illustrate a single channel of mobility in each polarity IMS, it is understood that the mobility cells can also be multi-channeled mobility cells as described in this application and in the following: U.S. Pat. No. 6,683,299 to Fuhrer et al.; in copending application Ser. No. 10/155,291 to Fuhrer et al. filed on Oct. 20, 2003; and in the U.S. application of Fuhrer et al. filed on Oct. 18, 2003 and having application Ser. No. 10/967,715. All of the aforementioned patents and patent applications are incorporated by reference as though fully described herein. Thus there is an instrument which allows high mass and mobility resolution of simultaneously laser-desorbed ions and post-ionized laser-desorbed neutrals. This configuration is obviously not restricted to the analysis of aerosol particles. For example the entraining of ions and neutrals desorbed from a surface as described already in paragraph [112] can be accomplished so that the gas stream is directed between the two mobility cells. This is particularly useful for microprobe imaging of a surface and allows the time width of the desorbing radiation which impinges a surface to be comparable to the drift time of the entraining gas flow which can be many 10's of microseconds depending on gas pressures and flow conditions. This approach is particularly effective when the two mobility cells have multiple channels allowing collection of ions from a several cm long gas flow between the two opposing mobility cells.

Addition of Repulsively Biased Conical Electrode to Improve Focusing of Ions Through Multiaperture Double Electrode Structures FIG. 6C illustrates the addition of a third biasable element which is made of electrically connected small cones which are positioned above the solid "web" region between the multiapertures. Thus each composite mobility electrode structure comprises three biasable elements separated by thin insulator layers. An example is shown from a simulation in which 10 eV positive ions of mass 720 are drifted through 2 Torr of helium toward the composite multiaperture mobility electrode. The conical electrode element is biased as indicated to a +8.3 eV repulsive potential which serves to repel the ions away from the "web" region where they would otherwise collide and be lost if the conical structure were not there. The ions are deflected by the combination of this field and by the gas flow into the apertures. The deflected ions are then transmitted by the attractive potential provided by the two electrode couplet which provide field penetration from the back electrode into the center of the aperture. All biases would be reversed for the purpose of transmitting negative ions.

It should be understood that this conical biasable element can be added to any of the multi-aperture structures previously described and thus improve transmission through these devices. Although the conical structure may be made of any conductor or semiconductor, it may also comprise an insulator thin film. This insulator thin film would initially charge as the first few ions come through the mobility cell and thereafter would serve to repel subsequent ions through the multi-apertures. An alternative structure would have the conical structure fabricated from thin film piezoelectric structures (which themselves could be coated with a thin dielectric film) which could be biased to produce a surface dipole which would act to repel approaching ions.

Another embodiment would make each electrode from flexible circuit board copper-kapton-copper material. Desired hole arrays would either be punched or laser drilled into a cut coupon of the material so that the electrical isolation of the front and back copper was maintained. Electrical connection to the front and back isolated copper electrodes could be formed by known circuit board etching techniques. The coupons could then be aligned and sandwiched together in a mechanical jig and mold into which epoxy would be poured and cured. The high vacuum epoxy would make a suitable vacuum seal and the intimate electrical contact of the back of one coupon to the face of the next would eliminate any of the exposed web areas and would thus form small individual ion mobility columns each of which could be used to resolve its own stream of ions. The electrical biasing of each element would be easily done by a combination of power supplies and resistors applied to the leads which would emerge from the hardened epoxy housing. The interface region (120) of FIGS. (26A and 26B) can also be made by this technique. The interface region (120) can also be located outside of the vacuum housing containing the skimmer and differential pumping capability.

An ideal multibore IMS cell would feed each of its channels directly into a multihole skimmer and thence into the oTOFMS or it could also be fed through an RF mulitpole cooling apparatus as shown in FIG. 28 which serves to keep the output of each channel spatially separated and substantially parallel as each goes into an ion detection device which may be a oTOFMS equipped with a position sensitive detector.

Multi-channel Ion Interface

Figure 28A:
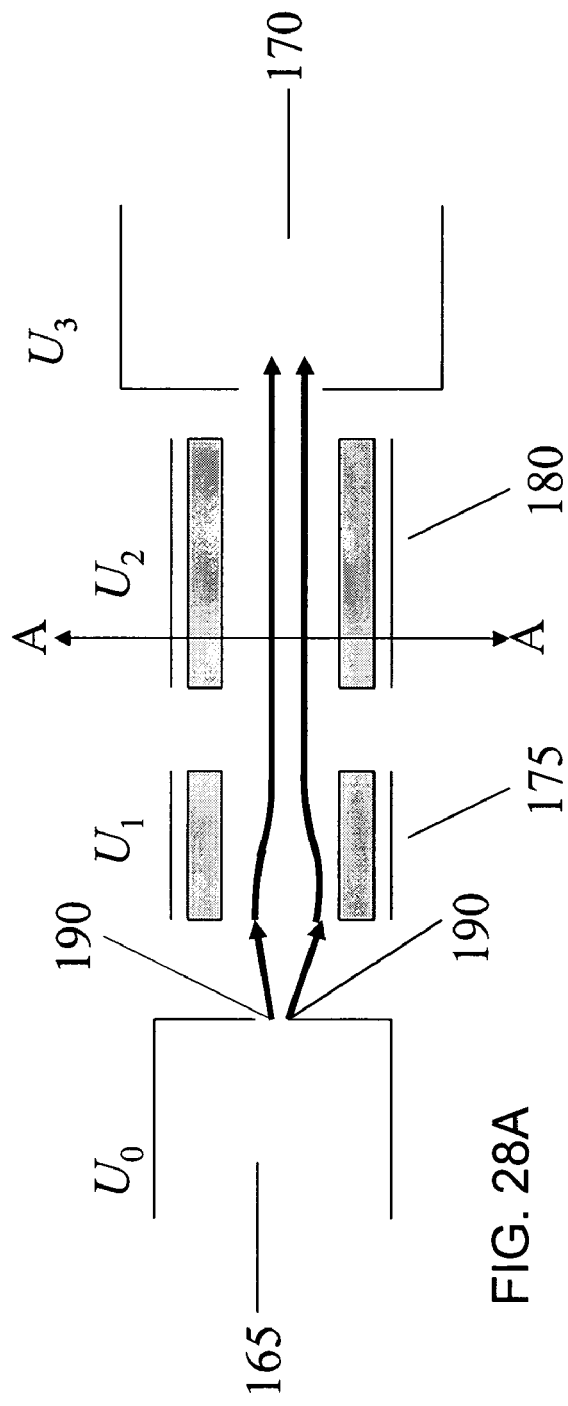
FIG. 28. 28A: Schematic view of RF interface between mobility cell and mass spectrometer; 28B: Cross-sectional view of one RF interface region.
Figure 28B:
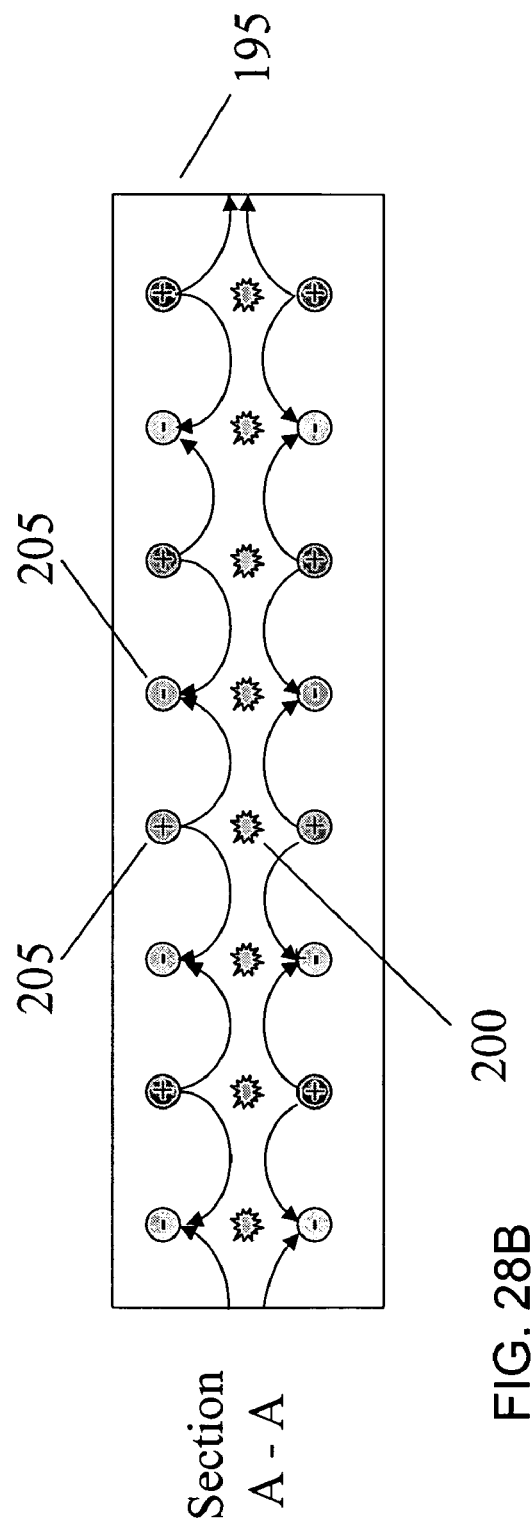

Another embodiment of the invention, illustrated in FIGS. 28A and 28B, combines a multi-channel RF interface between the exit of the multi-channel mobility cell (165) and the input to the extraction region of the MS (170). Between the mobility cell (165) and the MS (170) is a multi-stage RF focusing interface (components (175) and (180) in the example of the drawings illustrating two stages). Ions (190) exit the mobility cell (165) and enter the RF interface region. In FIG. 28B, a cross-sectional view of the second RF region (180 from FIG. 28A; also referred to as section A—A)) is shown. The multiple ion beamlets which emerge from the multiple channels of the IM cell and interface assembly can be directed through one or more stages of gas filled RF multipole ion guide. FIG. 28B shows eight separate ion beamlets (one of which is labeled as (200)) traversing the section RF stage shown in cross-section. Each beamlet is directed into its own two stages of an RF multi-pole multi-channel ion guide assembly. The number of optical elements chosen in FIG. 28 is arbitrary and one skilled in the art will realize that many additional elements can be added to a typically sized TOF instrument. The assembly has a rectangular envelope (195) and sixteen rods (205) located as shown in the cross-sectional view of FIG. 28B. In FIG. 28 each of the two rectangular envelopes (one for each RF stage in FIG. 28) and the sixteen rods in each stage are electrically connected to a common DC potential and so have the same DC potential for acceleration of ions coming into each stage. The rods additionally are supplied by RF-voltages of opposite phases and the same amplitude (+U sin $\omega$t and −U sin $\omega$t). Ions are focused to positions around the points of zero RF-field.

A particularly useful and powerful embodiment of this device is for the case when ions have been separated on the basis of their charge to volume ratio by an IMS cell prior to their entering the RF interface. In this case the amplitude or frequency of the RF field can be continuously optimized to maximize the transmission of the particular charge to volume ratio which is present at any particular time relative to the start of the IMS separation. This is very useful for MALDI-IMS experiments in which the singly ionized charge state is predominant. IMS of familial classes of biomolecules have been found to have a predictable relationship between the charge to volume and the charge to mass of each ion in the familial class. This relationship is different for most familial classes of singly charge biomolecular ions (e.g., lipids, peptides, oligonucleotides) so that each ion of a familial class lies along a distinct familial "trend line" in the two dimensional plot of mobility drift time vs. m/z. Thus, the time of arrival of an ion with a particular m/z can be predicted by the familial trend line and the mobility drift time (which is related to the ion's volume to charge ratio) so the RF amplitude, or frequency can be continuously computer controlled and optimized for the transmission of the specific m/z of each ion in the familial trend line. Thus, the RF field would have optimal characteristics for low m/z values at the start of the IM separation and very different field characteristics as the larger m/z ions eluted from the IM cell at longer mobility drift times. An approximately linear increase of m/z values along a familial trend line occurs. It is a reasonable approximation to increase the amplitude of the RF-voltage which is applied to the rods to be proportional to the square root of the time measured relative to a zero time when the initiation of the ionization event occurs. The coefficient of proportionality is the slope of the familial trend line. Such a time changing RF-field thus synchronized to the elution of ions at the end of the mobility cell would allow to record small ions without defocusing and losing them due to possible instability of their motion for large RF-fields necessary for the focusing and transport of larger ions. Also it would allow the effective focusing of ions of large masses for essentially the same width ion beams for ions of all masses. Since multi-charged ions would be focused even better than for the singly charged ions such an approach will focus all ions well below 1 mm diameter ion beams as the corresponding simulations show. The length and the number of the sections and the DC voltages applied to them should be found by computer simulation for providing enough time for desired ion focusing without losing of their separation received before in mobility cell and without decomposing of the ions. Any broadening of the mobility resolution because of the increased residence time of ions in the RF assembly could be almost completely removed by numerical deconvolution of the mobility resolved spectra after first determining—either experimentally or theoretically—the residence time as a function of mass of the ions within the RF assembly.

An RF-field ion focusing gives ions additional energy of ion motion in the plane orthogonal to axis being equal to the ion thermal energy. See, for example, Raznikov, et al RCM V 15, 1912–1921 (2001). If the axial velocity of ions is small in comparison with average thermal velocity of helium (~1300 m/sec) then the thermal energy of ions corresponds to the room temperature and it is about 0.013 eV per 1 degree of freedom. Of interest here is the degree of freedom which lies in the plane of the channels of our ion guide orthogonal to the direction of ion motion which due to RF-field contribution wherein we would have about 0.026 eV energy. For the energy of ion motion in the axial direction 26 eV which is typical for ions coming into the TOF MS then the divergence angle on average would be about 0.03 rad. The ion beams would, on average, be 6 mm wide after traveling 10 cm. The distance between ion beams of 6 mm and the width of recording plate 50 mm would be enough for recording the output of eight individual channels.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An apparatus comprising:
an ion source,
a first ion mobility drift cell, said first ion mobility drift cell having an entrance fluidly coupled to the ion source, said first ion mobility drift cell comprising at least two electrode pairs having an intra-electrode gap between individual electrodes of a pair which is smaller than an inter-electrode gap between electrode pairs, and an exit.

2. The apparatus of claim 1, wherein electrodes near the exit of the ion mobility cell have greater thickness than electrodes further removed from the exit of the ion mobility cell.

3. The apparatus of claim 1, wherein the electrodes near the exit of the ion mobility cell are of smaller diameter than electrodes further removed from the exit of the ion mobility cell.

4. The apparatus of claim 1, wherein the electrodes near the exit of the ion mobility drift cell have one or more apertures comparable in dimension to the dimensions of the exit.

5. The apparatus of claim 1, wherein one or more electrode pairs near the entrance of the ion mobility cell have smaller outside diameter than one or more electrode pairs farther away from the entrance.

6. The apparatus of claim 5, wherein the first several sets of electrodes near the entrance of the ion mobility cell have an increasing outside diameter in the direction of said exit.

7. The apparatus of claim 1, further comprising an RF voltage and a dc electrode voltage, wherein said RF voltage is superimposed on said dc electrode voltage.

8. The apparatus of claim 1, further comprising a time-of-flight mass spectrometer fluidly coupled to the exit of the mobility drift cell by way of an orthogonal extractor and a low energy monochromatized electron beam coupled to said orthogonal extractor.

9. The apparatus of claim 1, wherein the exit comprises a plurality of apertures.

10. The apparatus of claim 9, wherein the plurality of apertures is comprised of a 4033 circular array of apertures, the array having a diameter of 5.37 mm and a total aperture area of 8 mm$^2$.

11. The apparatus of claim 1, wherein one or more electrodes in the drift cell has a plurality of apertures.

12. The apparatus of claim 11, wherein the distribution of apertures in the electrodes changes from said entrance to said exit.

13. The apparatus of claim 12, wherein the distribution of apertures changes from a circular distribution to a horizontal rectangle distribution.

14. The apparatus of claim 1, wherein the exit is at least partially coated with a thin insulating film.

15. The apparatus of claim 14, wherein the insulating film comprises piezoelectric film.

16. The apparatus of claim 1, wherein one or more electrodes comprise piezoelectric thin films.

17. The apparatus of claim 1, wherein said first mobility drift cell has one or more collision induced dissociation regions within it.

18. The apparatus of claim 17, wherein the collision induced dissociation region is placed near the exit of said mobility drift cell.

19. The apparatus of claim 17, wherein the collision induced dissociation region is placed near the center of said mobility drift cell.

20. The apparatus of claim 1, wherein the ion mobility drift cell further comprises at least one porous semiconductor electrode.

21. The apparatus of claim 20, where said at least one porous semiconductor electrode is located directly after the entrance.

22. The apparatus of claim 20, wherein said at least one porous semiconductor electrode is coated with a dielectric or piezoelectric thin film.

23. The apparatus of claim 1, where said ion source is a MALDI source.

24. The apparatus of claim 1, where said ion source is a secondary ion source.

25. The apparatus of claim 1, wherein one or more of said electrode pairs are replaced with electrodes triads.

26. The apparatus of claim 1, wherein at least one of said electrodes is a multiaperture conical skimmer electrode.

27. The apparatus of claim 1, further comprising
a differentially pumped interface fluidly coupled to said ion mobility drift cell;
a conical skimmer fluidly coupled to said differentially pumped interface;
an extractor fluidly coupled to said conical skimmer; and,
a time-of-flight mass spectrometer fluidly coupled to said extractor.

28. The apparatus of claim 1, further comprising
a differentially pumped interface fluidly coupled to said ion mobility drift cell;
a multihole skimmer fluidly coupled to said differentially pumped interface;
an extractor fluidly coupled to said multihole skimmer; and,
a time-of-flight mass spectrometer fluidly coupled to said extractor.

29. The apparatus of claim 1, wherein said ion mobility drift cell forms part of a multibore ion mobility spectrometer.

30. The apparatus of claim 1, wherein at least one of said electrode pairs is comprised of flexible copper-kapton-copper material.

31. The apparatus of claim 1, further comprising
a multichannel RF interface fluidly coupled to said drift cell;
an extractor fluidly coupled to said multichannel RF interface; and,
a time-of flight mass spectrometer fluidly coupled to said extractor.

32. The apparatus of claim 1, further comprising:
an second ion mobility drift cell fluidly coupled to said first ion mobility drift cell, said second ion mobility drift cell comprising electrode pairs having an intra-electrode gap which is smaller than an inter-electrode gap between electrode pairs; and,
a differentially pumped interface fluidly coupled to said second ion mobility drift cell.

33. The apparatus of claim 32, further comprising
a conical skimmer fluidly coupled to said differentially pumped interface;
an extractor fluidly coupled to said conical skimmer; and,
a time-of-flight mass spectrometer fluidly coupled to said extractor.

34. The apparatus of claim 32, wherein one or more of said electrode pairs of said first ion mobility drift cell, said second ion mobility drift cell, or both, are replaced with electrodes triads.

35. An apparatus comprising:
a source of ion or neutral species,
a first and second ion mobility drift cell, said first and second ion mobility drift cells being substantially horizontally opposed to one another and fluidly coupled to said source, wherein one or both of said ion mobility drift cells comprise at least two electrode pairs having an intra-electrode gap between individual electrodes of a pair which is smaller than an inter-electrode gap between electrode pairs, and,
a first mass spectrometer fluidly coupled to said first ion mobility drift cell and a second mass spectrometer fluidly coupled to said second ion mobility drift cell.

36. The apparatus of claim 35 further comprising a fragmentation source positioned to fragment ions and neutral species entering one or both of said first and second ion mobility drift cells.

37. The apparatus of claim 35 where said first mass spectrometer, said second mass spectrometer, or both, are time-of-flight mass spectrometers.

38. A method of analyzing ion according to their mobility in a gas comprising:
a first ionization step to form ions from an analytical sample,
introducing said ions into a mobility drift cell, said mobility drift cell having a separation axis,
applying regions of alternating high and low electric field along the separation axis of the drift cell, said regions of alternating high and low electric field resulting from an electrode configuration, said electrode configuration comprising at least two electrode pairs having an intra-electrode gap between individual electrodes of a pair which is smaller than the inter-electrode gap between electrode pairs, and detecting ions.

39. The method of claim 38, further comprising the step of applying an RF voltage superimposed on a dc electrode voltage along at least a part of said separation axis.

40. The method of claim 38, further comprising the step of changing the charge of ions after said step of applying.

41. The method of claim 38, wherein said step of detecting comprises detecting with a mass spectrometer.

42. The method of claim 41, wherein said mass spectrometer is a time-of-flight mass spectrometer.

43. The method of claim 42, further comprising the step of RF focusing of said ions before said step of detecting with a time-of-flight mass spectrometer.

44. The method of claim 38, wherein the step of said first ionization comprises forming ions using a MALDI ion source.

45. The method of claim 38, wherein the step of said first ionization comprises forming ions using a secondary ion source.

46. The method of claim 38, wherein the step of said first ionization comprises forming ions using a electrospray ionization combined with an ion trap.

47. The method of claim 38, further comprising a second ionization step.

48. The method of claim 38, wherein said step of applying regions of alternating high and low electric field comprises applying two substantially horizontally opposed regions of alternating high and low electric field through the use of two substantially horizontally opposed ion mobility drift cells.

49. The method of claim 48, wherein said step of detecting comprises detecting with a mass spectrometer.

50. The method of claim 49 wherein said step of detecting with a mass spectrometer comprises detecting with a time-of-flight mass spectrometer.

* * * * *